(12) United States Patent
Rubalcaba, Jr. et al.

(10) Patent No.: US 11,395,875 B2
(45) Date of Patent: Jul. 26, 2022

(54) USER INTERFACE IMPROVEMENTS FOR MEDICAL DEVICES

(71) Applicant: ICU Medical, Inc., San Clemente, CA (US)

(72) Inventors: Bernardino Rubalcaba, Jr., Escondido, CA (US); Mihaela Cozmi, Gilroy, CA (US); Glenn Davis, Grayslake, IL (US); Angela LeCaptain, Silver Lake, WI (US); Angela Marino, Deerfield, IL (US); Raymond P. Silkaitis, Lake Forest, IL (US); H. Clay Teel, IV, San Diego, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 16/859,837

(22) Filed: Apr. 27, 2020

(65) Prior Publication Data
US 2020/0357500 A1 Nov. 12, 2020

Related U.S. Application Data

(63) Continuation of application No. 12/337,803, filed on Dec. 18, 2008, now Pat. No. 10,635,784.
(Continued)

(51) Int. Cl.
*A61M 5/142* (2006.01)
*G06F 8/60* (2018.01)
(Continued)

(52) U.S. Cl.
CPC ........... *A61M 5/14212* (2013.01); *G06F 8/60* (2013.01); *G16H 20/17* (2018.01); *A61M 5/1452* (2013.01);
(Continued)

(58) Field of Classification Search
CPC ........ G16H 40/63; G16H 20/17; G16H 70/40; A61M 2205/3561; A61M 5/142; A61M 2205/505; A61M 2205/6009; A61M 2205/6018; A61M 2205/6072; Y10S 707/99939
See application file for complete search history.

(56) References Cited

U.S. PATENT DOCUMENTS 3,894,431 A 7/1975 Muston et al.
5,014,798 A 5/1991 Glynn
(Continued)

FOREIGN PATENT DOCUMENTS

CA 2 113 473 3/1993
CA 2 551 817 7/2005
(Continued)

*Primary Examiner* — Phenuel S Salomon
(74) *Attorney, Agent, or Firm* — Knobbe Martens Olson & Bear, LLP

(57) ABSTRACT

A method and system is disclosed for operating a medical device with or without a cassette in place. A method is disclosed for adding additional VTBI to an ongoing infusion without stopping the infusion and with maintaining the infusion parameters. A method and system is disclosed for changing the CCA without having to interrupt or completely stop an ongoing infusion. Quick titration buttons are provided to allow improved navigation between various delivery display screens.

9 Claims, 41 Drawing Sheets

Related U.S. Application Data

(60) Provisional application No. 61/014,677, filed on Dec. 18, 2007.

(51) Int. Cl.
  *G16H 20/17* (2018.01)
  *A61M 5/145* (2006.01)
  *G16H 70/40* (2018.01)

(52) U.S. Cl.
  CPC ..... *A61M 5/14228* (2013.01); *A61M 5/14232* (2013.01); *A61M 2205/3561* (2013.01); *A61M 2205/3592* (2013.01); *A61M 2205/505* (2013.01); *G06T 2200/24* (2013.01); *G06T 2219/2016* (2013.01); *G16H 70/40* (2018.01); *Y10S 128/06* (2013.01)

(56) References Cited

U.S. PATENT DOCUMENTS

| | | | |
|---|---|---|---|
| 5,368,562 A * | 11/1994 | Blomquist | A61M 5/172 604/246 |
| 5,772,635 A * | 6/1998 | Dastur | G16H 40/63 604/67 |
| 7,976,508 B2 | 7/2011 | Hoag | |
| 8,075,514 B2 | 12/2011 | Butterfield et al. | |
| 8,180,440 B2 | 5/2012 | McCombie et al. | |
| 8,905,965 B2 | 12/2014 | Mandro et al. | |
| 9,539,383 B2 | 1/2017 | Kohlbrecher | |
| 9,545,475 B2 | 1/2017 | Borges et al. | |
| 10,463,788 B2 | 11/2019 | Day | |
| 10,578,474 B2 | 3/2020 | Ruchti et al. | |
| 10,596,316 B2 | 3/2020 | Dumas, III et al. | |
| 10,635,784 B2 | 4/2020 | Rubalcaba, Jr. et al. | |
| 10,656,894 B2 | 5/2020 | Fryman | |
| 2003/0018289 A1 * | 1/2003 | Ng | G16H 40/67 604/6.01 |
| 2004/0128163 A1 | 7/2004 | Goodman et al. | |
| 2005/0108057 A1 * | 5/2005 | Cohen | G16H 20/17 705/3 |
| 2005/0119597 A1 * | 6/2005 | O'Mahony | A61M 25/0028 604/4.01 |
| 2006/0136095 A1 | 6/2006 | Rob et al. | |
| 2006/0229557 A1 * | 10/2006 | Fathallah | G16H 40/63 604/131 |
| 2006/0255149 A1 * | 11/2006 | Retter | G06K 7/1095 235/462.41 |
| 2007/0094045 A1 | 4/2007 | Cobbs et al. | |
| 2007/0250339 A1 | 10/2007 | Mallett et al. | |
| 2009/0105636 A1 | 4/2009 | Hayter et al. | |
| 2009/0114037 A1 | 5/2009 | Smith | |
| 2009/0119330 A1 | 5/2009 | Sampath et al. | |
| 2010/0317952 A1 | 12/2010 | Budiman et al. | |
| 2011/0218514 A1 | 9/2011 | Rebours | |
| 2011/0313390 A1 | 12/2011 | Roy et al. | |
| 2012/0089411 A1 * | 4/2012 | Srnka | G09F 3/10 705/2 |
| 2012/0323212 A1 | 12/2012 | Murphy | |
| 2013/0032634 A1 * | 2/2013 | McKirdy | G06Q 30/0271 235/375 |
| 2013/0044111 A1 | 2/2013 | VanGilder et al. | |
| 2014/0145915 A1 * | 5/2014 | Ribble | A61G 7/002 345/8 |
| 2014/0180711 A1 | 6/2014 | Kamen et al. | |
| 2015/0065988 A1 | 3/2015 | Holderle et al. | |
| 2015/0371004 A1 * | 12/2015 | Jones | G16H 20/17 705/2 |
| 2016/0151601 A1 | 6/2016 | Cardelius et al. | |
| 2020/0069864 A1 | 3/2020 | Shubinsky et al. | |
| 2020/0090122 A1 | 3/2020 | Hume | |
| 2020/0238007 A1 | 7/2020 | Day | |

FOREIGN PATENT DOCUMENTS

| | | |
|---|---|---|
| EP | 1 490 131 | 12/2007 |
| WO | WO 2004/070994 | 8/2004 |
| WO | WO 2009/141504 | 11/2009 |
| WO | WO 2012/108910 | 8/2012 |
| WO | WO 2017/144366 | 8/2017 |

* cited by examiner

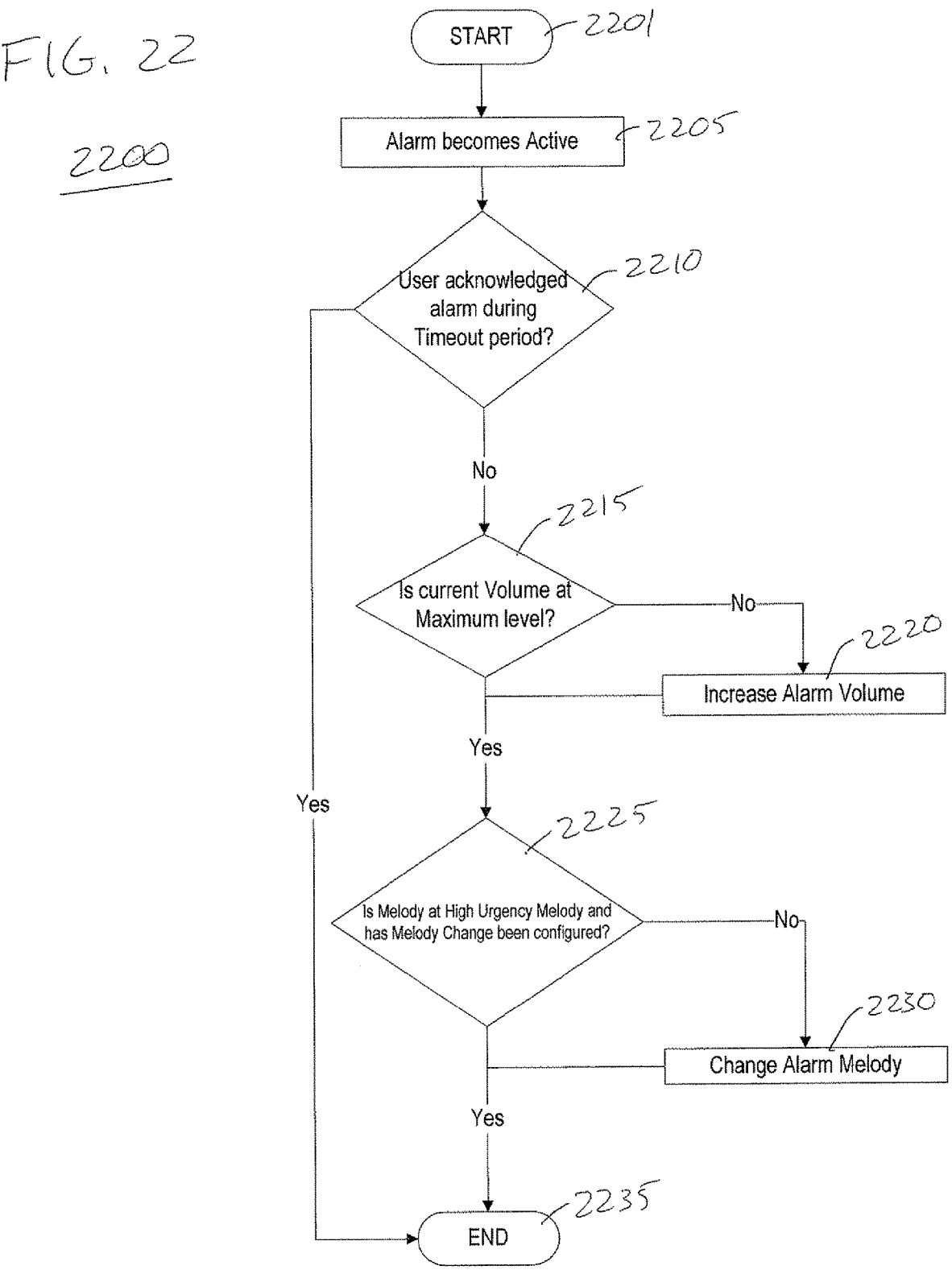

USER INTERFACE IMPROVEMENTS FOR MEDICAL DEVICES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention relates to medical devices. More specifically, the invention relates to infusion pumps that include touch screen graphical user interfaces.

BACKGROUND OF THE INVENTION

Graphical user interfaces for medical devices that display patient and treatment information have improved clinician efficiency when caring for patients. However, a challenge for designing graphical user interfaces is the need to balance the amount of information displayed on any one screen viewable be the clinician with the need to create a device that is easy to read and navigate. Too often the user is presented with an overwhelming amount of information, impeding the interaction between the user and the user interface.

Additionally, medical devices, including medical pumps, can be complicated and time-consuming for caregivers to program. The need for an improved graphical interface is critical to maintain efficiency of patient care and to reduce potential clinical errors and thereby improve patient safety. Device interfaces that increase input efficiency and accuracy are critical to improve patient safety and therapy.

Graphical user interface design must also take into account strict design parameters as well as safety parameters. As a result, many medical devices do not provide flexibility in programming parameters, neither for the administrator nor for the clinician.

Therefore, it would be desirable to have a medical device that includes a graphical user interface that is easier to navigate, that allows for easier programming of the medical device and that increases efficiency and accuracy of the clinician programming and navigation.

To that end, it is an object of the invention to provide a medical device that is programmable with or without a cassette in place.

It is another object of this invention to provide a medical device wherein a change in clinical care area can be programmed without interruption of an ongoing infusion.

It is another object of this invention to provide a medical device that allows an additional volume to be infused (VTBI) to be programmed before the completion of an ongoing infusion.

It is another object of this invention to provide a medical device with improved navigation buttons.

It is another object of this invention to provide a medical device that allows the clinician to configure the display of infusion data.

It is another object of this invention to provide a medical device with improved alarm features.

It is a further object of the invention to provide a configurable dose-back calculation feature.

SUMMARY OF THE INVENTION

A method and apparatus system is disclosed for operating a medical device with or without a cassette in place. A method is disclosed for adding additional VTBI to an ongoing infusion without stopping the infusion and with maintaining the infusion parameters. A method and system is disclosed for changing the CCA without having to interrupt or completely stop an ongoing infusion. Quick titration buttons are provided to allow improved navigation between various delivery display screens.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

FIG. 22 is a flow chart for a program for responding to various call back alarms, in accordance with the present invention;

DETAILED DESCRIPTION OF THE PREFERRED EMBODIMENT

Figure 1:
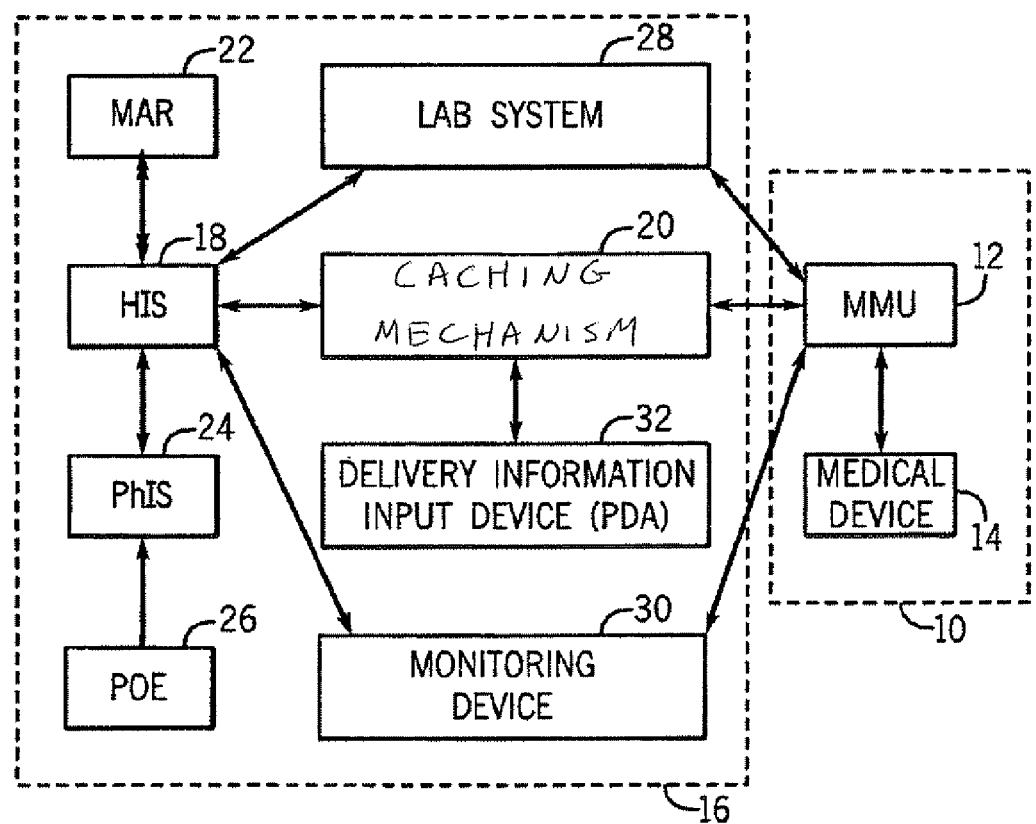
FIG. 1 is a schematic diagram of the medication management system including a medication management unit and a medical device, integrated with an information system, in accordance with the present invention.

The present invention will be described as it applies to its preferred embodiment. It is not intended that the present invention be limited to the preferred embodiment. It is intended that the invention cover all modifications and alternatives that may be included within the scope of the appended claims With reference to FIG. 1, the medication management system (MMS) 10 of the present invention includes a medication management unit (MMU) 12 and a medical device 14, typically operating in conjunction with one or more information systems or components of a hospital environment 16. The term hospital environment should be construed broadly herein to mean any medical care facility, including but not limited to a hospital, treatment center, clinic, doctor's office, day surgery center, hospice, nursing home, and any of the above associated with a home care environment. As discussed below, there can be a variety of information systems in a hospital environment. As shown in FIG. 1, the MMU 12 communicates to a hospital information system (HIS) 18 via a caching mechanism 20 that is part of the hospital environment 16.

It will be understood by those of skill in art that the caching mechanism 20 is primarily a pass through device for facilitating communication with the HIS 18 and its functions can be eliminated or incorporated into the MMU 12 (FIG. 1) and/or the medical device 14 and/or the HIS 18 and/or other information systems or components within the hospital environment 16. The caching mechanism 20 provides temporary storage of hospital information data separate from the HIS 18, the medication administration record system (MAR) 22, pharmacy information system (PhIS) 24, physician order entry (POE) 26, and/or Lab System 28. The caching mechanism 20 provides information storage accessible to the Medication Management System 10 to support scenarios where direct access to data within the hospital environment 16 is not available or not desired. For example, the caching mechanism 20 provides continued flow of information in and out of the MMU 12 in instances where the HIS 18 is down or the connectivity between the MMU 12 and the electronic network (not shown) is down.

The HIS 18 communicates with a medication administration record system (MAR) 22 for maintaining medication records and a pharmacy information system (PhIS) 24 for delivering drug orders to the HIS. A physician/provider order entry (POE) device 26 permits a healthcare provider to deliver a medication order prescribed for a patient to the hospital information system directly or indirectly via the PhIS 24. One skilled in the art will also appreciate that a medication order can be sent to the MMU 12 directly from the PhIS 24 or POE device 26. As used herein the term medication order is defined as an order to administer something that has a physiological impact on a person or animal, including but not limited to liquid or gaseous fluids, drugs or medicines, liquid nutritional products and combinations thereof.

Lab system 28 and monitoring device 30 also communicate with the MMU 12 to deliver updated patient-specific information to the MMU 12. As shown, the MMU 12 communicates directly to the lab system 28 and monitoring device 30. However, it will be understood to those of skill in art that the MMU 12 can communicate to the lab system 28 and monitoring device 30 indirectly via the HIS 18, the caching mechanism 20, the medical device 14 or some other intermediary device or system.

Delivery information input device 32 also communicates with the MMU 12 to assist in processing drug orders for delivery through the MMU 12. The delivery information input device 32 can be any sort of data input means, including those adapted to read machine readable indicia such as barcode labels; for example a personal digital assistant (PDA) with a barcode scanner. Hereinafter the delivery information input device 32 will be referred to as input device 32. Alternatively, the machine readable indicia may be in other known forms, such as radio frequency identification (RFID) tag, two-dimensional bar code, ID matrix, transmitted radio ID code, human biometric data such as fingerprints, etc. and the input device 32 adapted to "read" or recognize such indicia. The input device 32 is shown as a separate device from the medical device 14; alternatively, the input device 32 communicates directly with the medical device 14 or may be integrated wholly or in part with the medical device.

Figure 2:
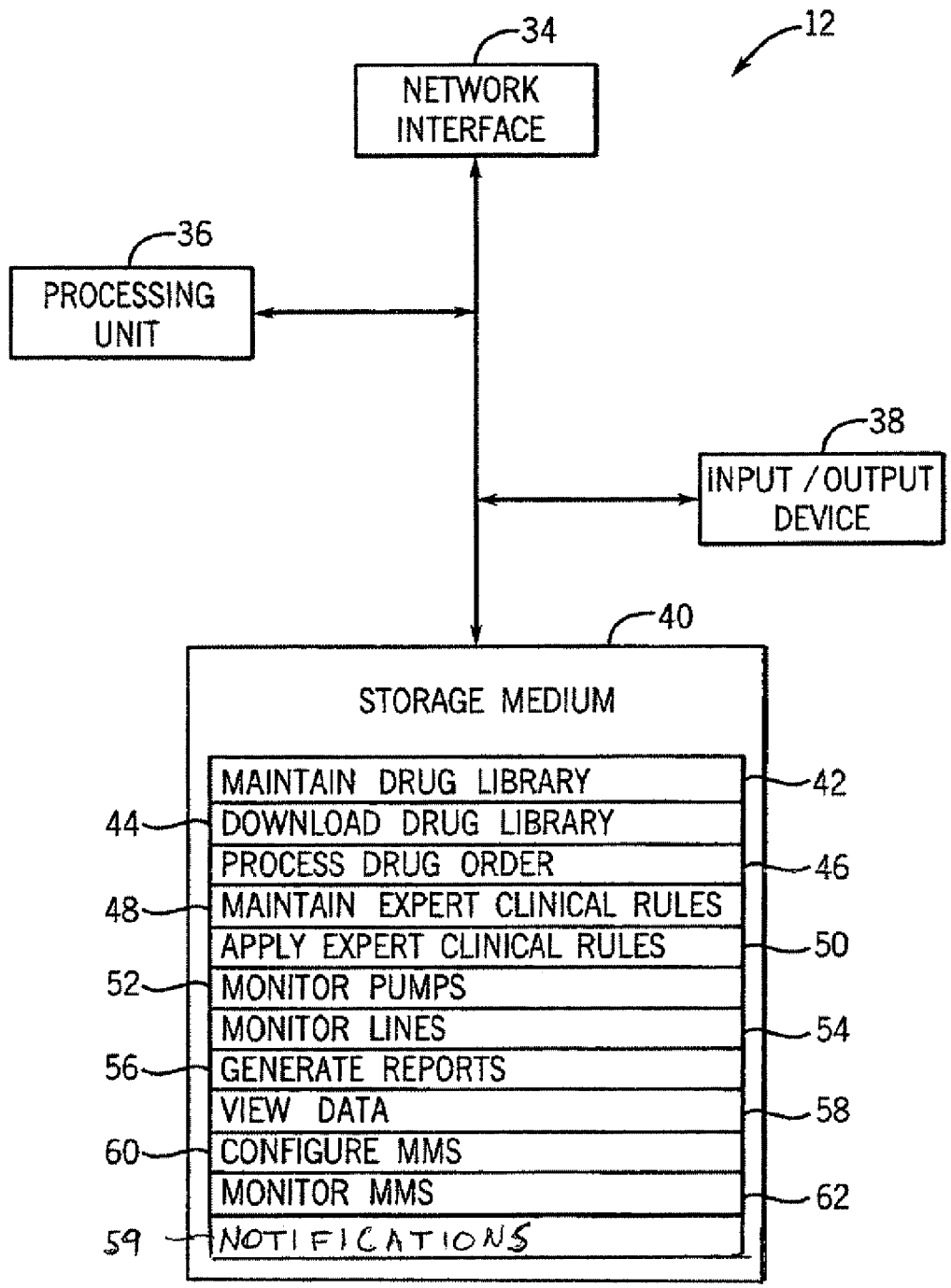
FIG. 2 is a schematic diagram of the medication management unit, in accordance with the present invention.

With reference to FIG. 2, the medication management unit 12 includes a network interface 34 for connecting the MMU 12 to multiple components of a hospital environment 16, one or more medical devices 14, and any other desired device or network. A processing unit 36 is included in MMU 12 and performs various operations described in greater detail below. A display/input device 38 communicates with the processing unit 36 and allows the user to receive output from processing unit 36 and/or input information into the processing unit 36. Those of ordinary skill in the art will appreciate that display/input device 38 may be provided as a separate display device and a separate input device.

An electronic storage medium 40 communicates with the processing unit 36 and stores programming code and data necessary for the processing unit 36 to perform the functions of the MMU 12. More specifically, the storage medium 40 stores multiple programs formed in accordance with the present invention for various functions of the MMU 12 including but not limited to the following programs: Maintain Drug Library 42; Download Drug Library 44; Process Drug Order 46; Maintain Expert Clinical Rules 48; Apply Expert Clinical Rules 50; Monitor Pumps 52; Monitor Lines 54; Generate Reports 56; View Data 58; Configure the MMS 60; and Monitor the MMS 62. The Maintain Drug Library 42 program creates, updates, and deletes drug entries and establishes a current active drug library. The Download Drug Library 44 program updates medical devices 14 with the current drug library. The Process Drug Order 46 program processes the medication order for a patient, verifying that the point of care (POC) medication and delivery parameters match those ordered. The Maintain Expert Clinical Rules 48 program creates, updates, and deletes the rules that describe the hospital's therapy and protocol regimens. The Apply Expert Clinical Rules 50 program performs logic processing to ensure safety and considers other infusions or medication orders, patient demographics, and current patient conditions. The Monitor Pumps 52 program acquires ongoing updates of status, events, and alarms transmitted both real-time and in batch mode, as well as tracking the location, current assignment, and software versions such as the drug library version residing on medical device 14. The Monitor Lines 54 program acquires ongoing updates of status, events and alarms for each channel or line for a medical device 14 that supports multiple drug delivery channels or lines. The Generate Reports 56 program provides a mechanism that allows the user to generate various reports of the data held in the MMU storage medium 40. The View Data 58 program provides a mechanism that supports various display or view capabilities for users of the MMU 12. The Notifications 59 program provides a mechanism for scheduling and delivery of events to external systems and users. The Configure the MMS 60 program provides a mechanism for system administrators to install and configure the MMS 10. The Monitor the MMS 62 program enables information technology operations staff capabilities to see the current status of MMS 10 components and processing, and other aspects of day-to-day operations such as system start up, shut down, backup and restore.

Figure 3:
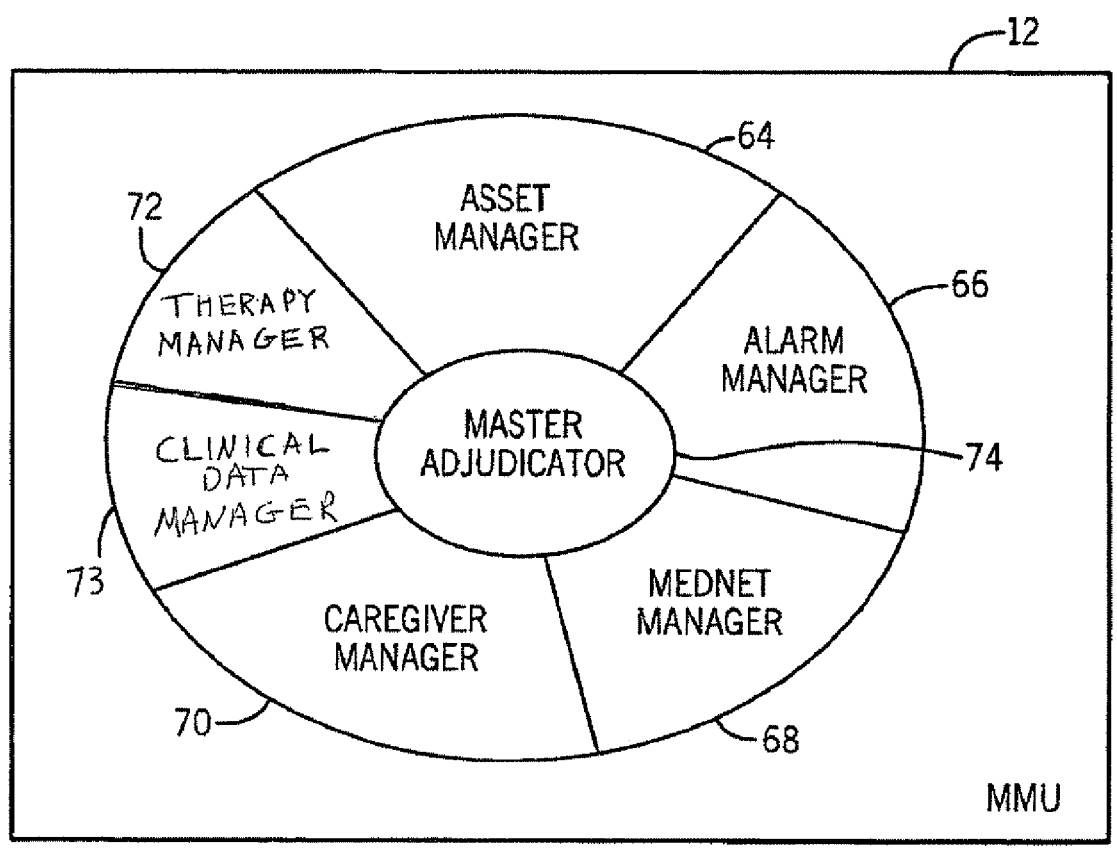
FIG. 3 is a schematic diagram illustrating some of the major functions performed by the medication management unit, in accordance with the present invention.

With reference to FIG. 3, the various functional programs 42-62 of the MMU 12, each including separate features and rules, are partitioned (at a higher level than shown in FIG. 2) and logically organized into interrelated managing units of the MMU 12. As shown, the MMU 12 includes an asset manager 64, an alarm manager 66, a drug library manager (such as, for example, is included in HOSPIRA MEDNET software) 68, a caregiver manager 70, a therapy manager 72, and/or a clinical data manager 73. However, one of ordinary skill in the art will appreciate that additional or alternative hospital system managing units can be provided without departing from the present invention. Additionally, the MMU 12 includes a master adjudicator 7 4 between the separate interrelated hospital system managing units 64-73 of the MMU 12, to regulate the interaction between the separate management units.

Further, while the MMU 12 as described herein appears as a single device, there may be more than one MMU 12 operating harmoniously and sharing the same database. For example the MMU 12 can consist of a collection of MMU specific applications running on distinct servers in order to avoid a single point of failure, address availability requirements, and handle a high volume of requests. In this example, each individual server portion of the MMU 12 operates in conjunction with other server portions of the MMU 12 to redirect service requests to another server portion of the MMU 12. Additionally, the master adjudicator 7 4 assigns redirected service requests to another server portion of the MMU 12, prioritizing each request and also ensuring that each request is processed.

With reference to FIGS. 2 and 3, the managing units 64-72 each include separate features and rules to govern their operation. For example, the asset manager 64 governs the execution of the Monitor Pumps 52 and Monitor Lines 54 programs; the drug library manager 68 governs the execution of the Drug Library 42 and Download Drug Library 44 programs; the therapy manager 72 governs the execution of the Process Drug Order 46, Maintain Expert Clinical Rules 48, and Apply Expert Clinical Rules 50 programs; and the clinical data manager 73 governs the execution of the Generate Reports 56 and View Data 58 programs. Other distribution of the functional MMU programs 42-62 among the hospital system managing units 64-73 can be made in accordance with the present invention.

Figure 4:
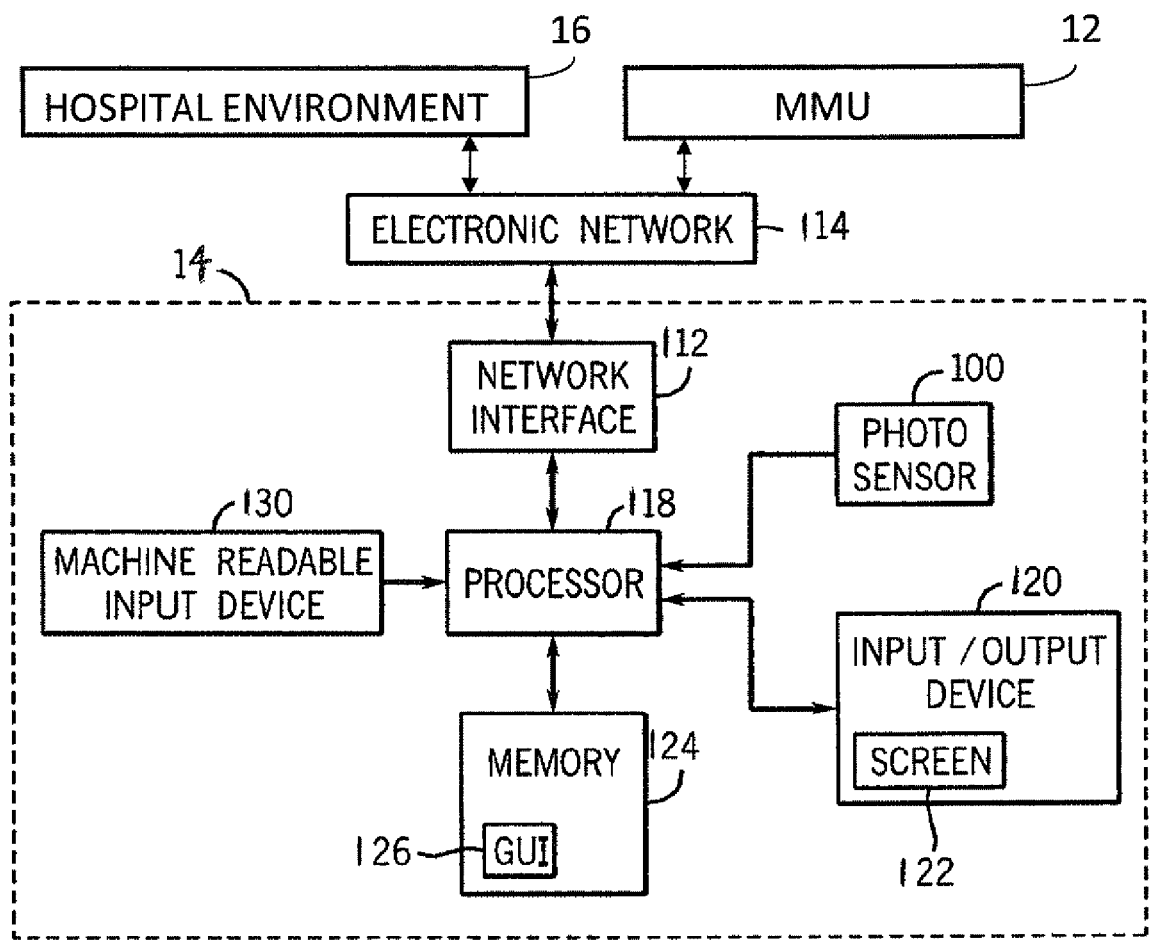
FIG. 4 is a schematic diagram of a medical device, in accordance with the present invention.

With reference to FIG. 4, an electronic network 114 connects the MMU 12, medical device 14, and hospital environment 16 for electronic communication. The electronic network 114 can be a completely wireless network, a completely hard wired network, or some combination thereof.

FIG. 4 is a schematic diagram illustrating several functional components of a medical device 14 for implementing the present invention. Those of ordinary skill in the art will appreciate that the device 14 includes many more components than those shown in FIG. 4. However, it is not necessary that all these components be shown in order to disclose an illustrative embodiment for practicing the present invention.

In the context of the present invention, the term "medical device" includes without limitation a device that acts upon a cassette, reservoir, vial, syringe, or tubing to convey medication or fluid to or from a patient (for example, an enteral pump, a parenteral infusion pump, a patient controlled analgesia (PCA) or pain management medication pump, or a suction pump), a monitor for monitoring patient vital signs or other parameters, or a diagnostic, testing or sampling device.

Figure 5:
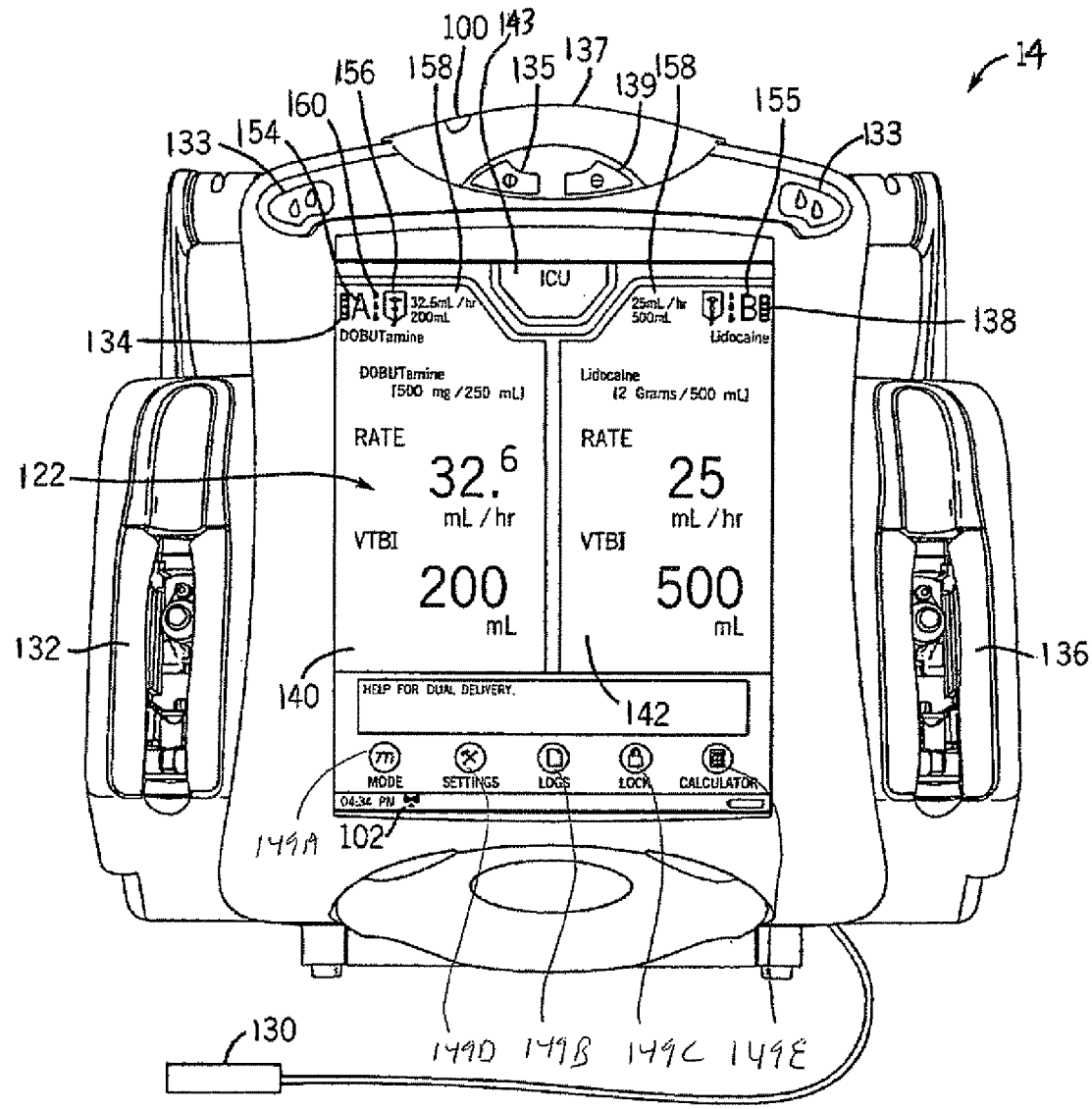
FIG. 5 is perspective view of a multi-channel medical device in communication with a machine-readable input device according to the present invention and shows a split screen display, having one portion associated with each channel, which is adapted to be displayed and viewed from afar during normal delivery of fluid, in accordance with the present invention.

With reference to FIG. 5, for the purpose of exemplary illustration only, the medical device 14 is disclosed as an infusion pump. More particularly, the medical device 14 can be a single channel infusion pump, a multi-channel infusion pump (as shown), or some combination thereof.

With reference to FIG. 4, the pump style medical device 14 includes a network interface 112 for connecting the medical device 14 to electronic network 114. Where a wireless connection to the electronic network 114 is desired, network interface 112 operates an antenna for wireless connection to the electronic network 114. The antenna can project outside the device 14 or be enclosed within the housing of the device.

A processor 118 is included in the medical device 14 and performs various operations described in greater detail below. The input/output device 120 allows the user to receive output from the medical device 14 and/or input information into the medical device 14. Those of ordinary skill in the art will appreciate that input/output device 120 may be provided as a single device such as a touch screen 122, or as a separate display device and a separate input device (not shown). In the preferred embodiment, the display screen 122 of the medical pump 14 is a thin film transistor active matrix color liquid crystal display with a multi-wire touch screen. A membrane generally impermeable to fluids overlays the display screen 122 so the user can press on images of keys or buttons on the underlying screen with wet gloves, dry gloves or without gloves to trigger an input.

A memory 124 communicates with the processor 118 and stores code and data necessary for the processor 118 to perform the functions of the medical device 14. More specifically, the memory 124 stores multiple programs formed in accordance with the present invention for various functions of the medical device 14 including a graphical user interface program 126 with multiple subparts described in greater detail below.

With reference to FIG. 5, the present invention provides a machine-readable input device 130. The machine-readable input device 130 communicates with the medical device 14 to input machine-readable information to the medical device 14. The machine-readable input device 130 can communicate, directly or indirectly, with the medical device 14 via a wireless or hard-wired connection. The machine-readable input device 130 can be a device that is separate from but associated or in communication with the medical device 14. The machine-readable input device 130 can be any sort of data input means, including those adapted to read machine-readable indicia, such as a barcode scanner or handheld personal digital assistant (PDA). Alternatively, the machine-readable input device 130 may be operable to read in other known forms of machine-readable information, such as radio frequency identification tags (RFID), touch memory, digital photography, biometrics, etc.

With reference to FIG. 5, the medical device 14 is a multichannel pump having a first channel 132 with first channel machine-readable label 134 and a second channel 136 with a second channel machine-readable label 138. A user of the medical device 14 operates the machine-readable input device 130 to select a channel from one or more channels 132 and 136, by scanning in the associated machine-readable label 134 or 138.

The user selects the desired channel 132 or 136 by using the machine-readable input device 130 to scan a factory or hospital programmed, unique, machine-readable label 134 or 138 that is electronically generated and presented on the screen 122, preferably juxtapositioned near the respective channel 132 or 136. Alternatively, the machine-readable labels 134 and 138 are physically affixed to the medical device 14, preferably on or juxtapositioned near the channel 132 and 136, respectively. Since the machine-readable labels 134 and 138 are generated and/or can be stored in memory 124 by the pump 14, the pump 14 can associate the machine-readable labels 134 and 138 to the channels 132 or 136. The pump 14 then allows the user to program and activate the selected channel 132 or 136. The user may also manually select the desired channel by touching an appropriate folder tab on the touch screen. The folder tabs are labeled and/or physically arranged on the screen so as to be proximate to the corresponding channel 132 or 136.

In a further aspect of the wireless embodiment, all the medical devices can periodically broadcast a unique wireless device/channel IP address and/or a self-generated unique machine-readable label (for example, a barcode) 134 or 138 that can also be presented on the screen 122. Alternatively, the machine-readable labels 134 and 138 are physically affixed to or posted on the medical device 14. Each medical device will correlate such broadcasted or posted device/channel IP addresses and/or barcodes with a particular patient, who is also identified by a unique machine readable label (not shown) or patient IP address. The user associates the desired pump(s) or channel(s) 132, 136 with the patient by using the machine-readable input device 130 to scan the unique machine-readable labels 134, 138 and the patient's machine readable label. This causes the appropriate pump processor(s) 118 to associate the appropriate pump channel(s) 132, 136 with the patient. Then the pumps or channels can associate, communicate, and coordinate with each other wirelessly.

Figure 17A:
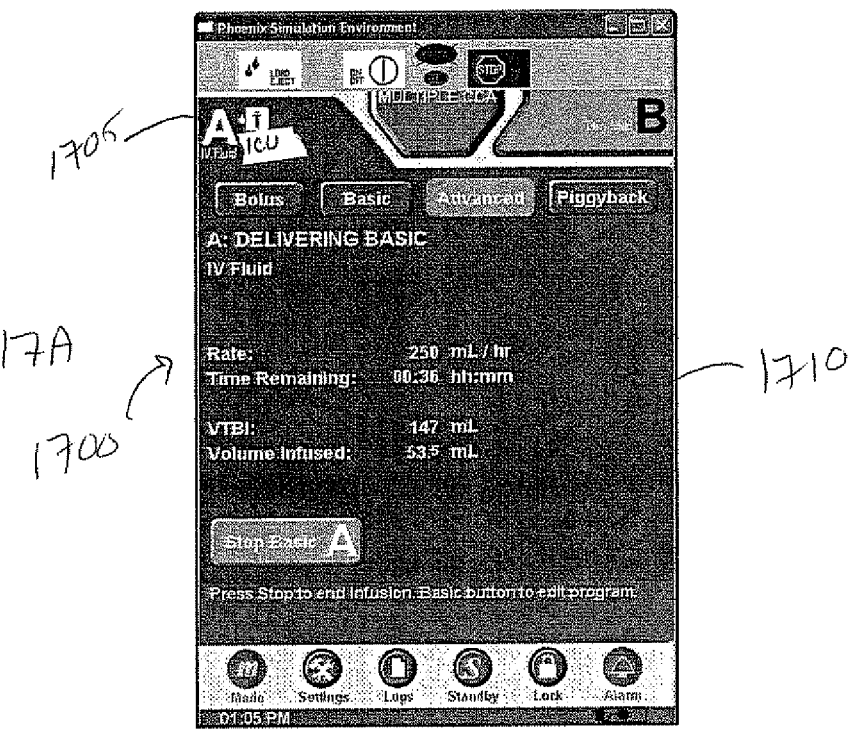
FIGS. 17A to 17C are screen shots illustrating a graphical user interface navigation button, in accordance with the present invention.
Figure 17B:
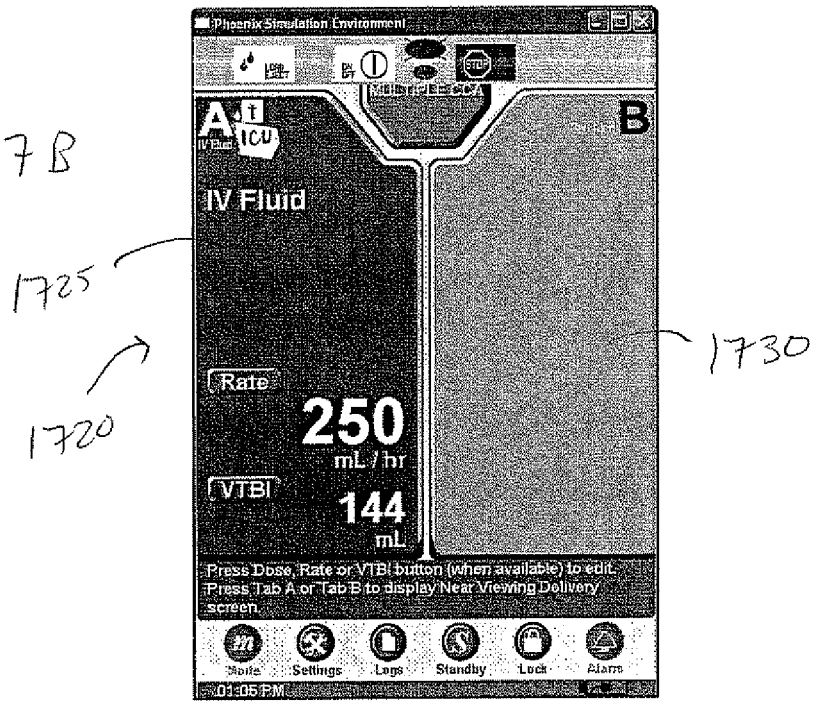

With reference to FIGS. 4, 5, 5A and 17A to 17C, the graphical user interface program 126 reallocates screen 122 for a medical device 14. Specifically, FIGS. 5 and 17B illustrates a multi-channel infusion pump 14 with a split touch screen 122 having a first channel screen portion 140 associated with first channel 132 and a second channel screen portion 142 associated with the second channel 136. Each channel screen portion 140 and 142 presents a subset of the delivery information regarding the respective channels 132 or 136, including without limitation therapeutic agent name, concentration, dose rate, VTBI, and alarm information, in a font size that it is easily readable by a user from a distance such as, for example, from approximately fifteen to twenty feet (4.6-6.2 meters) away. This is what is referred to as a "far view" delivery screen. The far view delivery screens display subsets of the information found on the relevant "near view" delivery screens, illustrated in FIGS. 17A and 17C. The near view delivery screen displays information such as, drug name, concentration, dose rate, time remaining, VTBI, volume remaining, and alarm name for the highest priority alarm if in an alarm state.

Figure 5A:
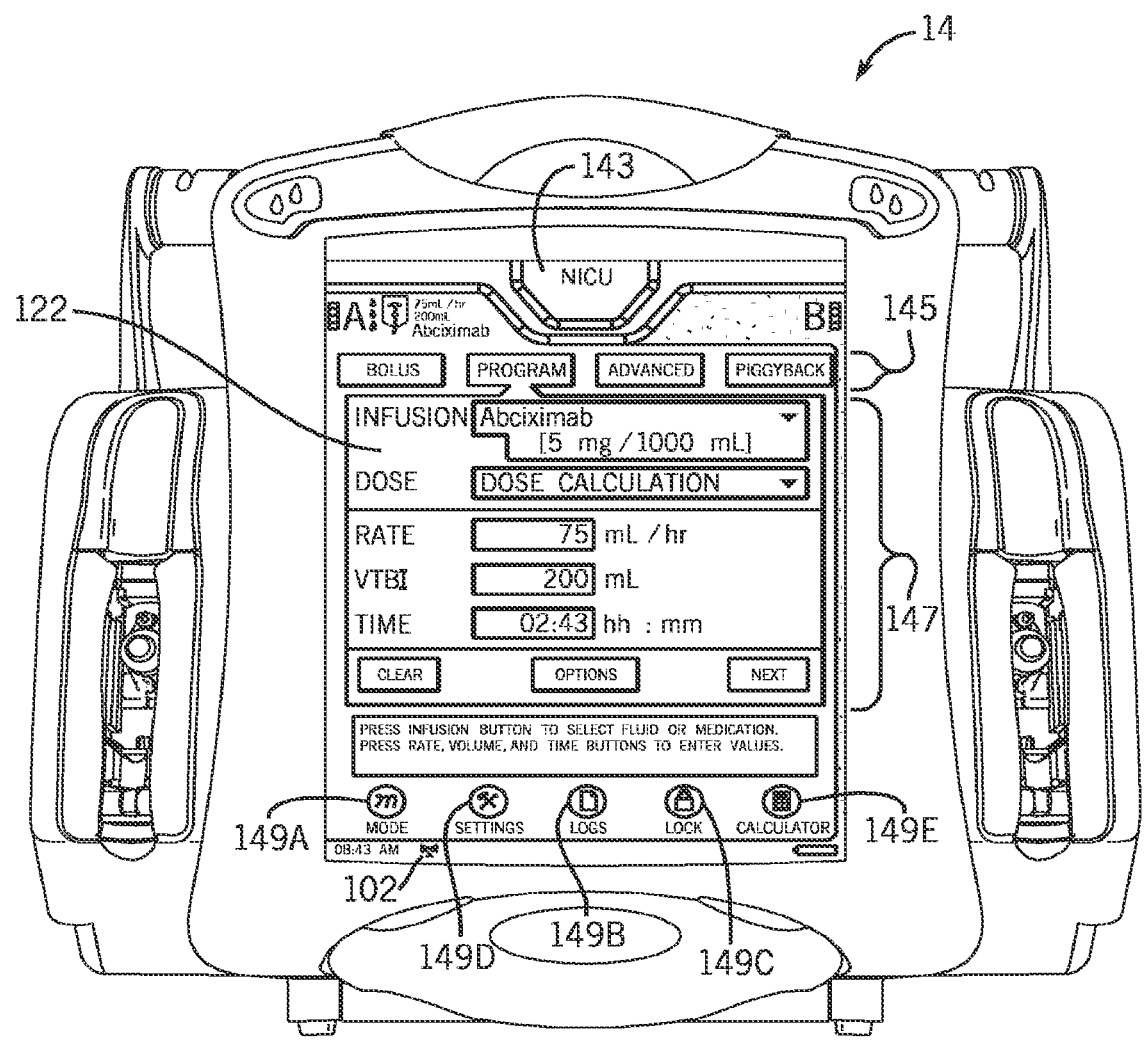
FIG. 5A is a perspective view similar to FIG. 5 and illustrates a near view display screen, in accordance with the present invention.
Figure 17C:
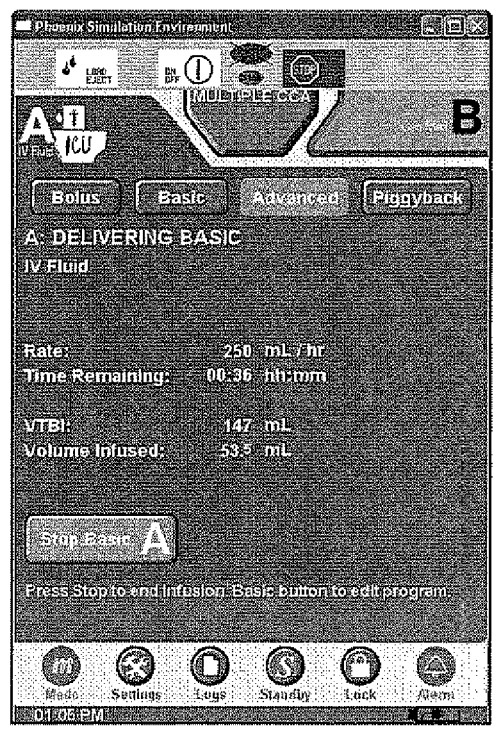

In practice, the delivery screen displays a near view when the user is programming the device as illustrated by FIG. 5A. The near view delivery screen will switch to the far view delivery screen after a predetermined period of time that is predetermined by the manufacturer, configurable by the facility via the drug library, and/or set by the caregiver at the pump, for example after 20 seconds. Often, the user does not want to wait for the predetermined length of time to view the far screen. FIGS. 17A to 17C illustrate one embodiment of a medical device that allows the user to switch from the near view screen to the far view screen and vice versa at any time, in accordance with the present invention. FIG. 17A illustrates a near view screen for channel A 1705. If, while in the near view screen, the user wants to view the far view screen, the user touches anywhere within the body 1710 of the near view screen. Touching the body 1710 of the near view screen displays the far view screen 1720 illustrated in FIG. 17B. Referring to FIG. 17B, upon a user touching one of the tabs "A" or "B" or anywhere on the channel screen portions 1725 or 1730 of the far view delivery screen, a "near view" delivery screen is presented on the screen (FIG. 17C). In one embodiment, the user touches a "hotspot" or special toggle button within the body of the current display screen to return to either the far view screen or the near view screen.

Figure 18:
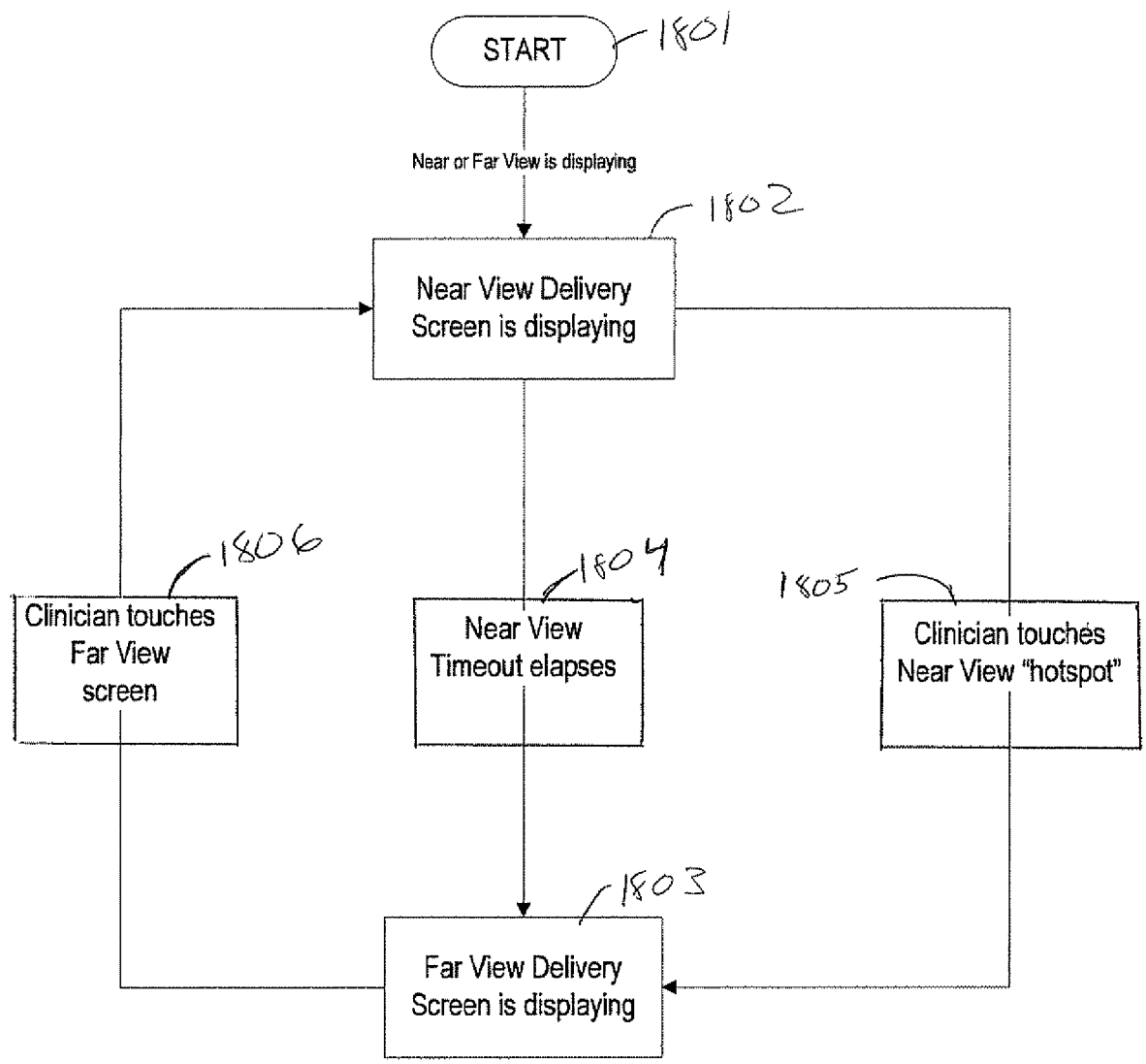
FIG. 18 is a flow chart for a program for determining a screen view display parameter, in accordance with the present invention.

Referring to FIG. 18, a flow chart for a program 1800 to immediately transition the display screen between the near view screen and the far view screen is illustrated. Program 1800 begins at block 1801 and progresses to block 1802 where the program determines that the near view delivery screen is displayed. In one aspect of the invention, program 1800 progresses in block 1804 to block 1803 when a near view time out elapses. In another aspect of the invention, program 800 moves from block 1802 to block 1803 when a user touches the near view hotspot in block 1805. Program 1800 may return to the near view screen, block 1802, from the far view screen, block 1803, when a user touches the far view screen in block 1806.

Returning to FIG. 5, the channel screen portion 140 or 142 selected or corresponding to the tab selected expands in area but the size of at least some of the text therein is shrunk, as shown in FIG. 17A The shrinkage of one of the channel screen portions 140 and 142 and enlargement of its counterpart provides additional space for one or more data display or data entry fields to be placed on screen 122, as shown in FIG. 5A. As discussed below, data displays or data entry fields are placed on screen 122 in space previously occupied by portions of the channel screen portion 140 or 142. This reallocation of space on screen 122 perm its the user to enter inputs more easily since the data entry field can be large, preferably at least as large or, more preferably, larger in area than the original channel screen portions 140 and 142 were in the delivery screen mode. Additionally, the reallocation of space on screen 122 provides greater space for presenting information on the channel being adjusted or monitored. Further details on the reallocation of screen 122 and the near view and far view delivery screens can be found in commonly owned and co-pending application U.S. Ser. No. 11/103,235 entitled USER INTERFACE IMPROVEMENTS FOR MEDICAL DEVICES filed on Apr. 11, 2005, which is expressly incorporated herein in its entirety.

Referring again to FIG. 5, pump 14 includes dedicated or fixed tactile infuser buttons, and images of buttons on the LCD-touch screen 122. The fixed tactile buttons 133, 135, 137, and 139 provide the following functions: LOAD/EJECT button 133—opens and closes the cassette carriage; ON/OFF button 135—turns power on and off; ALARM SILENCE button 137—silences a silenceable alarm for a specified period of time, for example two minutes; and EMERGENCY STOP button 139—stops all channels.

The LCD color touch screen 122 allows the user to access and use on-screen button images, for example 3D button images, and data entry fields. The touch screen 122 uses a membrane over the LCD display so a single keypress does not cause significant infusion pole movement nor is it mistaken for a double keypress. The touch screen also accommodates a keypress whether the user is wearing wet gloves, dry gloves, or no gloves.

LCD touch screen button images 143, 145, 147 and 149A-149E are located as shown in FIGS. 5 and 5A and perform the following functions: Patient Information Tab 143—displays the clinical care area, preselected patient information (including without limitation name, ID number, etc.), and provides access to a more detailed patient information screen (FIG. 9C); Channel Level Therapy Buttons 145—accessed by button images on the infuser touch screen, are used to select an infusion therapy; Program Level Buttons 147—accessed by pressing areas, drop-down list triangles, boxes or text boxes on the programming screen, are used to select dose parameters of an infusion; and Device Level Buttons 149A-149E at the bottom of the touch screen are used to display and control device level features, including without limitation Mode 149A (for example, Operational or Biomed), Logs 149B, Locks 149C, Settings 149D, and Calculator display 149E. A wireless indicator image 102 displayed at the bottom of the screen 122 indicates that the device 14 is connected and ready for communication.

By using the Channel Level Therapy Buttons 145 and the Program Level Buttons 147, the healthcare practitioner can program each individual channel of the pump with specific fluid therapies in a variety of weight and body surface area-based units such as micrograms/kg/hour, grams/m2/hr, and other delivery specifications for the following modes: Basic Therapy-includes dose calculation, which allows dose rate programming based on volume to be infused (VTBI), drug amount, infusion time and drug concentration and simple rate programming that allows programming of volumetric rate (ml/hr) based upon VTBI and time; Bolus delivery—allows user to program a single uninterrupted discrete delivery based on dose amount and time (the bolus can be delivered from the primary or a secondary container); Piggyback delivery—allows user to program the delivery of a secondary infusion, to be delivered through the same cassette as the primary infusion (the primary infusion is paused until the piggyback VTBI completes); and Advanced Programming. Advanced Programming mode provides various types of programs including: Multistep-which allows a sequential delivery of fluid in up to 10 steps, with fluid volumes and delivery rates programmable for each step based on Rate and Volume or Volume and Time; Variable Time—which allows up to 24 dose calculation steps at specified clock times; Intermittent—a calculated dose or step to be delivered at regular intervals; and Taper—a delivery that ramps up and/or ramps down to a plateau rate.

With reference to FIGS. 4 and 5, the graphical user interface 126 provides channel indicators presented on screen 122. The channel indicators associate on-screen programming, delivery, and alarm information with a particular delivery channel by using graphical depictions such as a channel indication icon 154, 155. The channel indication icon 154 or 155 is a graphical item clearly associating on-screen programming, delivery, and alarm information with a specified associated delivery channel. The channel indication icons 154 and 155 are located on a tab 158 associated with a specified delivery channel of the medical device The channel indication icon 154 or 155 may include but is not limited to a user readable letter or number, a machine-readable indicator 134, or a combination thereof. The graphical user interface program 126 also provides a drip indicator icon 160 and an infusion status icon 156 presented on screen 122.

Figure 19A:
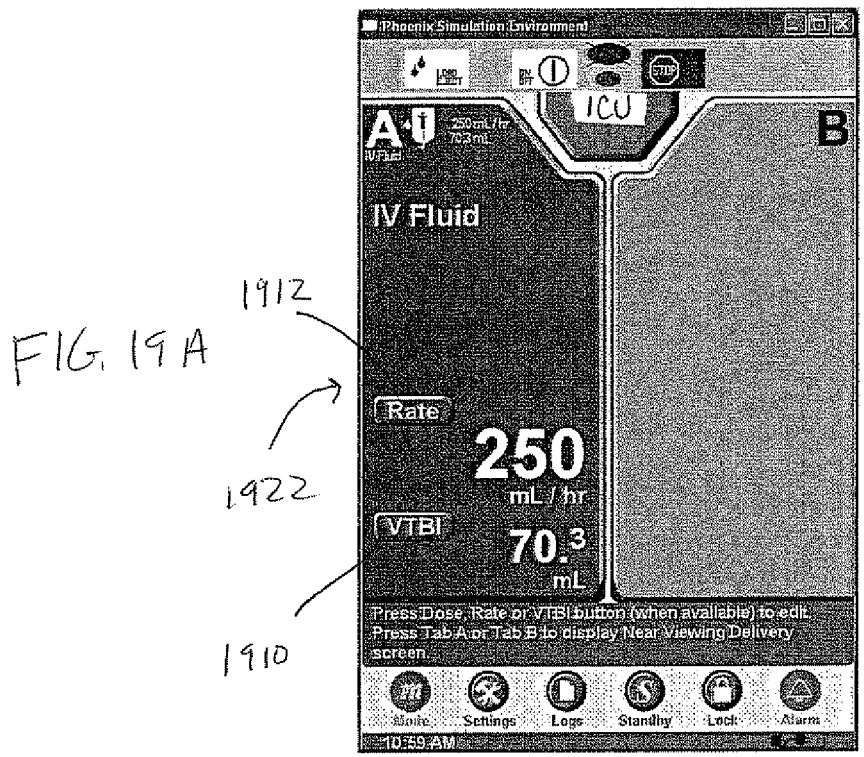
FIGS. 19A to 19G are screen shots illustrating additional graphical user interface navigation shortcut buttons, in accordance with the present invention.
Figure 19B:
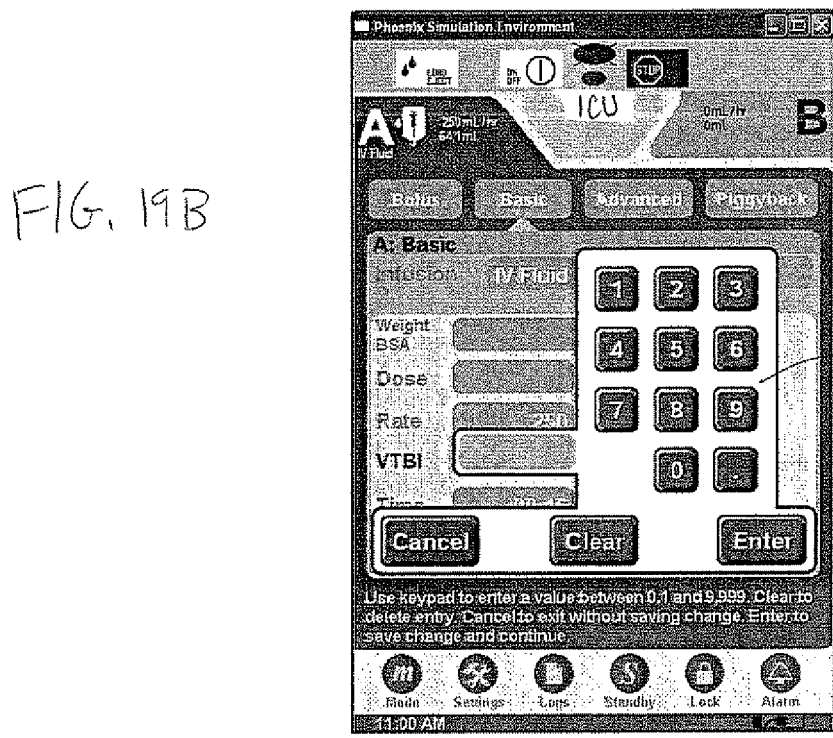
Figure 19C:
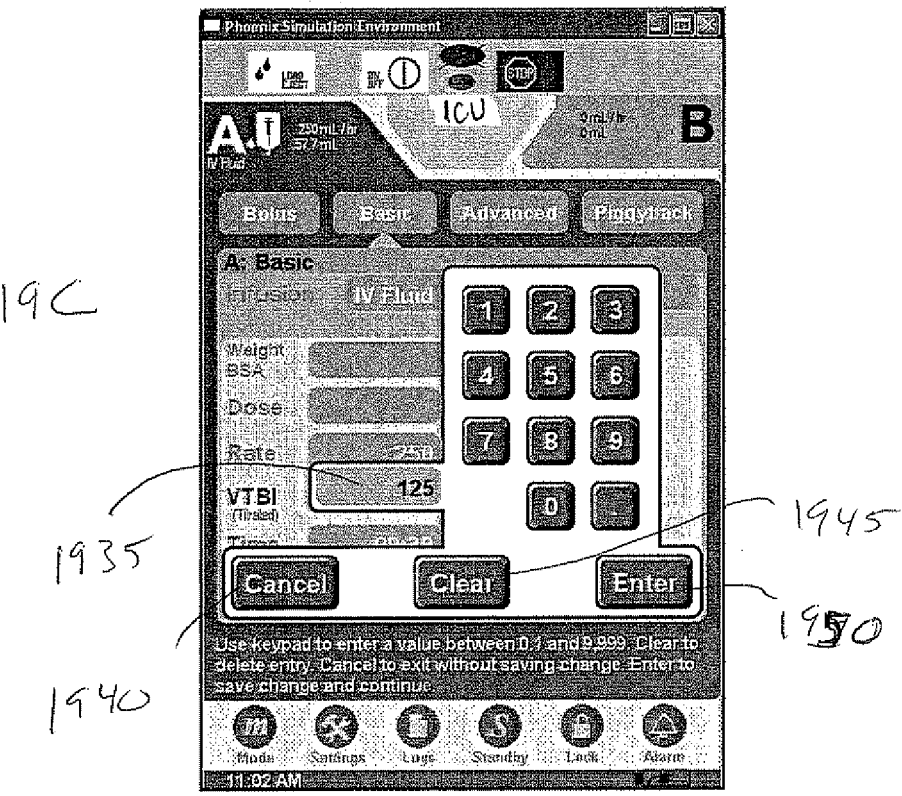
Figure 19D:
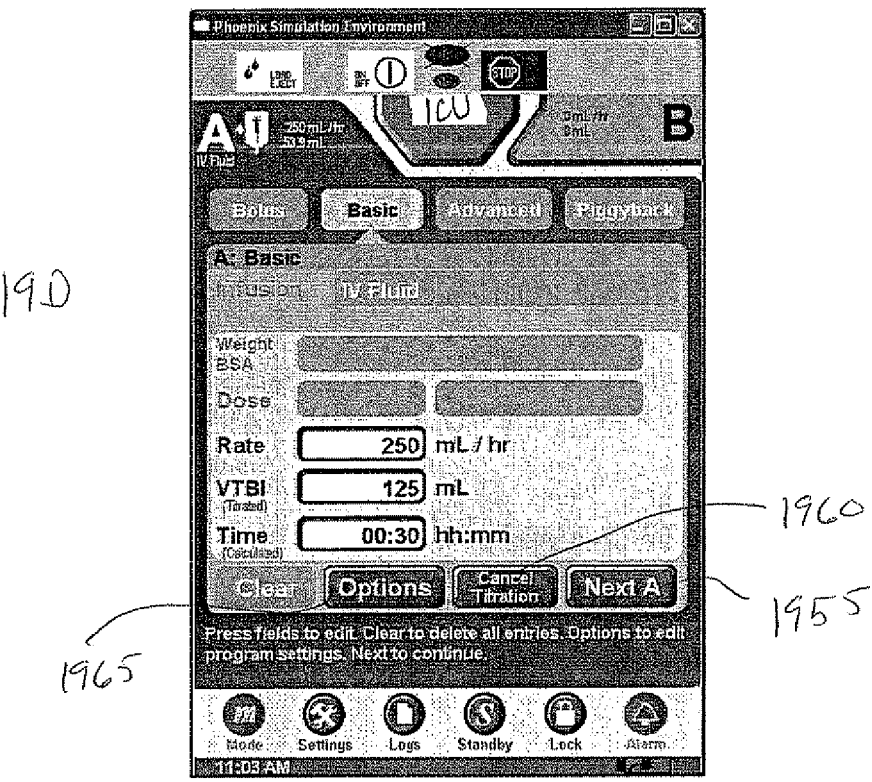
Figure 19E:
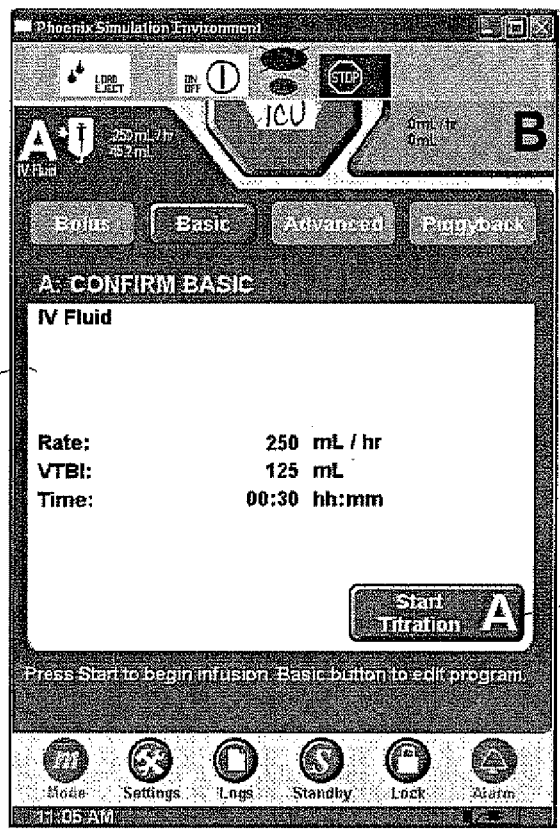
Figure 19F:
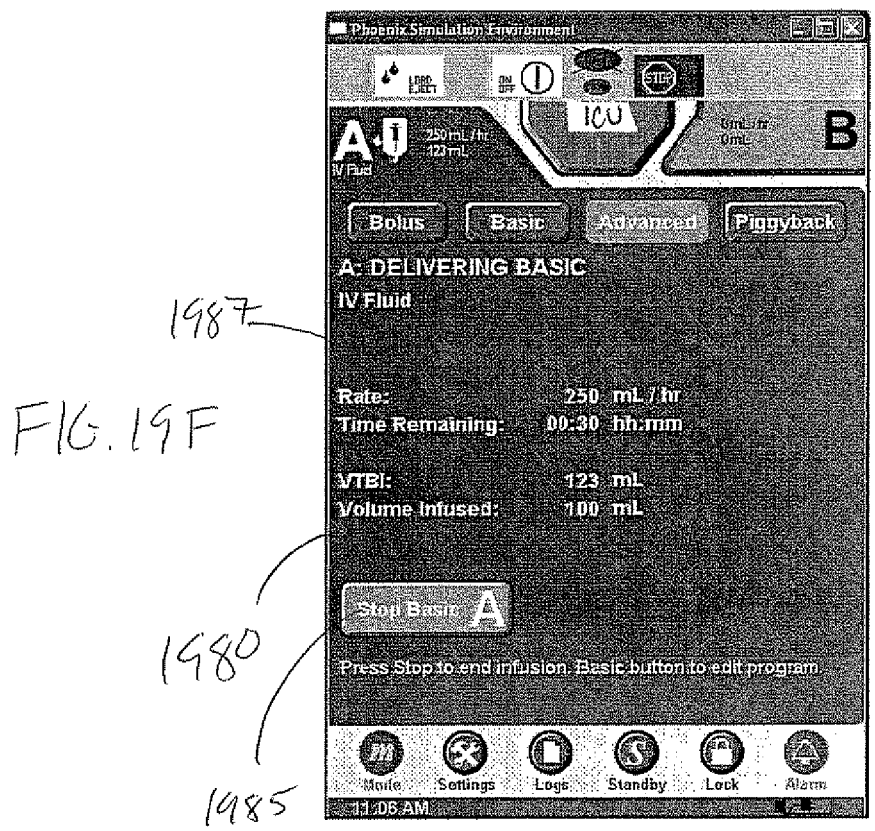
Figure 19G:
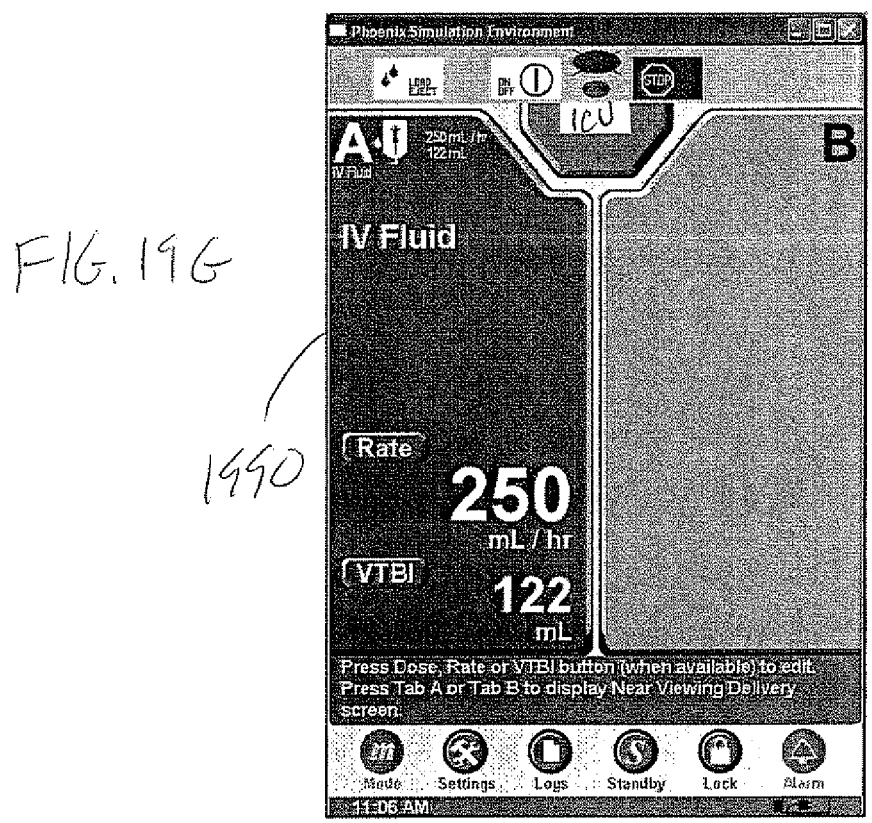

With reference to FIGS. 4, 5, 5A and 19A to 20, in one embodiment of the present invention, the graphical user interface 126 provides quick titration buttons 1910, 1912 presented on a far view screen 122, 1922. FIG. 19A illustrates quick titration buttons for VTBI 1910 and Rate 1912. In another or the same embodiment, graphical user interface 1922 may also have a quick titration button for "dose" or other titration parameters. Quick titration buttons 1910, 1912 operate as explode or active buttons that when pressed take a user to a standard data entry field for data entry when the button is selected. In this manner, with one press of a button the user can be quickly taken to the desired data entry location rather than having to back track through several screens as is common. The quick titration buttons, thus, increase the user's efficiency in programming the medical device in accordance with the present invention. FIGS. 19A to 19G illustrate the use of the VTBI quick titration button 1910. In practice, the user presses quick titration button 1910 (FIG. 19A) to bring up data entry field 1930 in FIG. 19B. In this embodiment, data entry field is a numerical keypad for entering a value for the VTBI. Once the desired value 1935 is entered, the user is prompted to use the keypad to cancel the entry by pressing the cancel button 1940, delete the entry by pressing the clear button 1945, or save the change and continue by pressing the enter button 1950 (FIG. 19C). FIG. 19D illustrates that the user pressed the enter button 1950 to accept and change the VTBI entry. At the graphical user interface illustrated in FIG. 19D, the user has the option to press "Next A" 1955 to continue, "Cancel Titration" 1960 to cancel the titration, or Options 1965 to edit the program. FIG. 19E illustrates that the user pressed "Next A" 1955 to continue. FIG. 19E illustrates a confirmation screen 1970. At this screen, the user is instructed to press "Start Titration A" 1975 to confirm the VTBI change and begin the infusion. At screen 1980 illustrated in FIG. 19F, the user can stop the titration by pressing "Stop Basic A" 1985. The near view screen 1980 illustrated in FIG. 19F returns to a far view screen 1990 shown in FIG. 19G.

Figure 20:
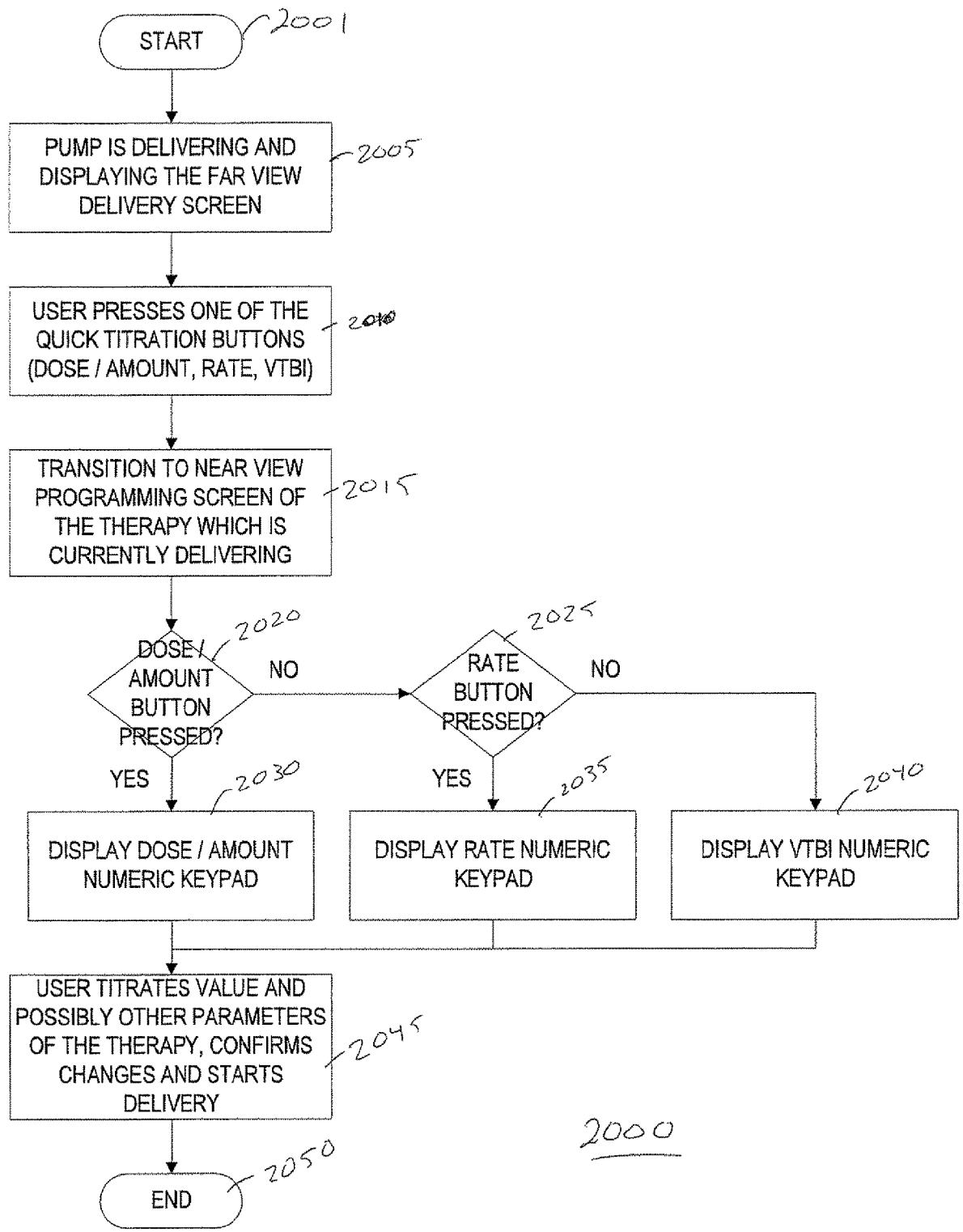
FIG. 20 is a flow chart for a program for determining a screen view display parameter based on the navigation shortcut buttons, in accordance with the present invention.

FIG. 20 is a flow chart of a program 2000 for operating quick titration buttons for "dose," "rate" and "VTBI" as discussed above. Program 2000 begins at block 2001 and progresses to block 2005 which indicates that the pump is delivering an infusion and displaying the far view delivery screen (see FIG. 19A). Program 2000 moves to block 2010 when a user presses one of the quick titration buttons 1910, 1912. In response to the pressing of the quick titration button, at block 2015 the program 2000 changes the display to the programming screen for the therapy which is currently delivering (e.g. Channel A or B). After the transition to the near view screen, program 2000 determines at blocks 2020 and 2025 which button was pressed. If the program determines that the Dose button was pressed the program displays the dose numeric keypad, block 2030. If the program determines that the rate button 1912 was pressed, the program displays the rate numeric keypad. If the program determines that neither the dose nor the rate button was pressed, the program displays the VTBI numeric keypad. Those with skill in the art will recognize that program 2000 can determine which button was pressed in any order other than that described herein. Once the keypad for the chosen button is displayed, the user inputs the desired data and continues with the program to confirm and run the infusion with the changed parameter as described above and illustrated in FIGS. 19A to 19G.

Figure 14:
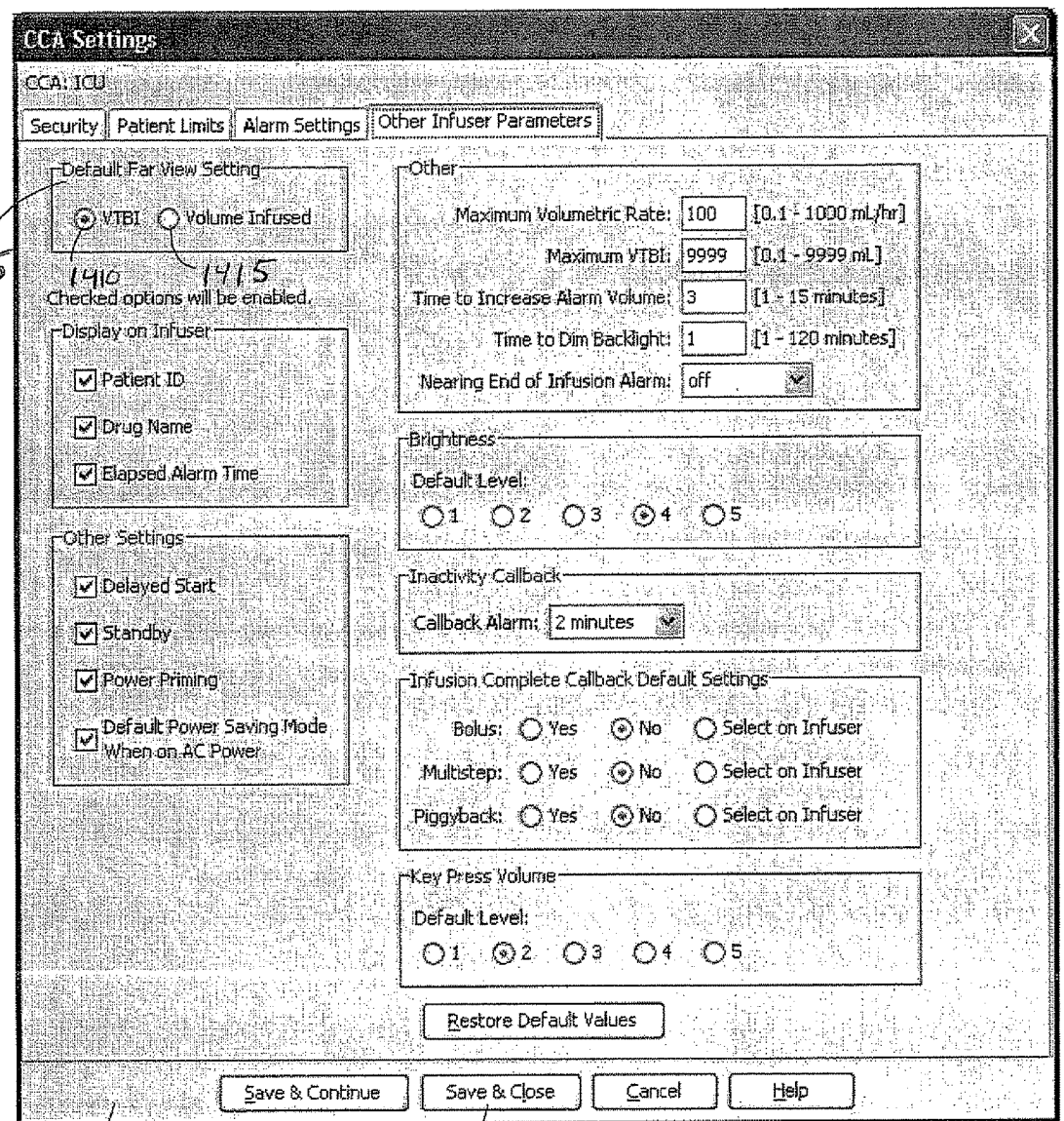
FIG. 14 is a screen shot of a graphical user interface for configuring a display setting at a drug library, in accordance with the present invention.
Figure 15A:
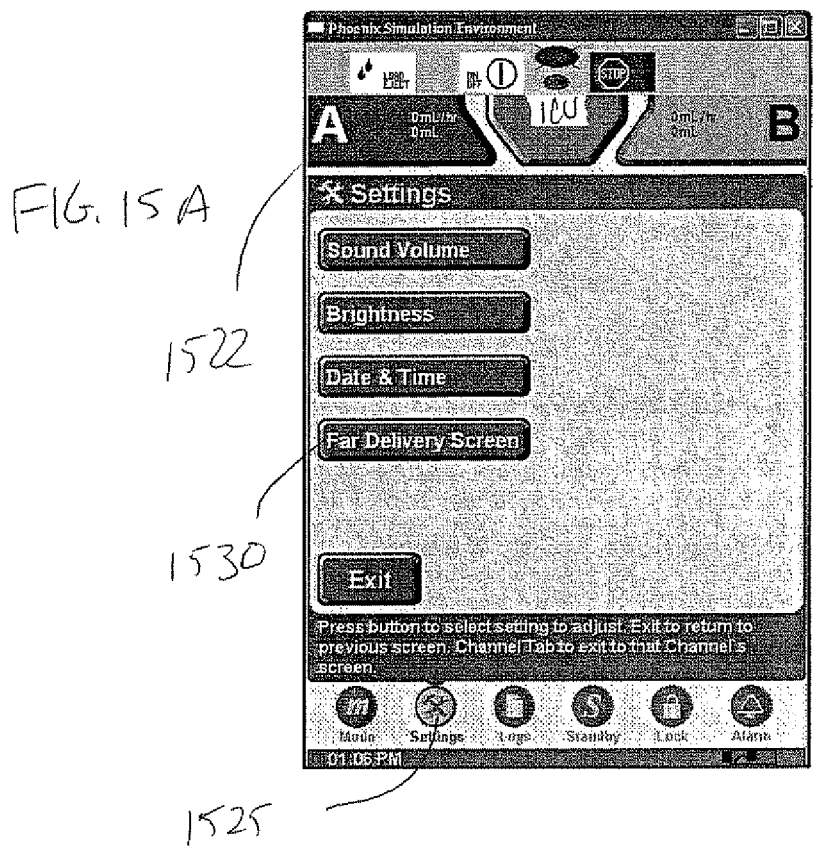
FIGS. 15A to 15C are screen shots illustrating a graphical user interface for configuring a medical device display parameter, in accordance with the present invention.
Figure 15B:
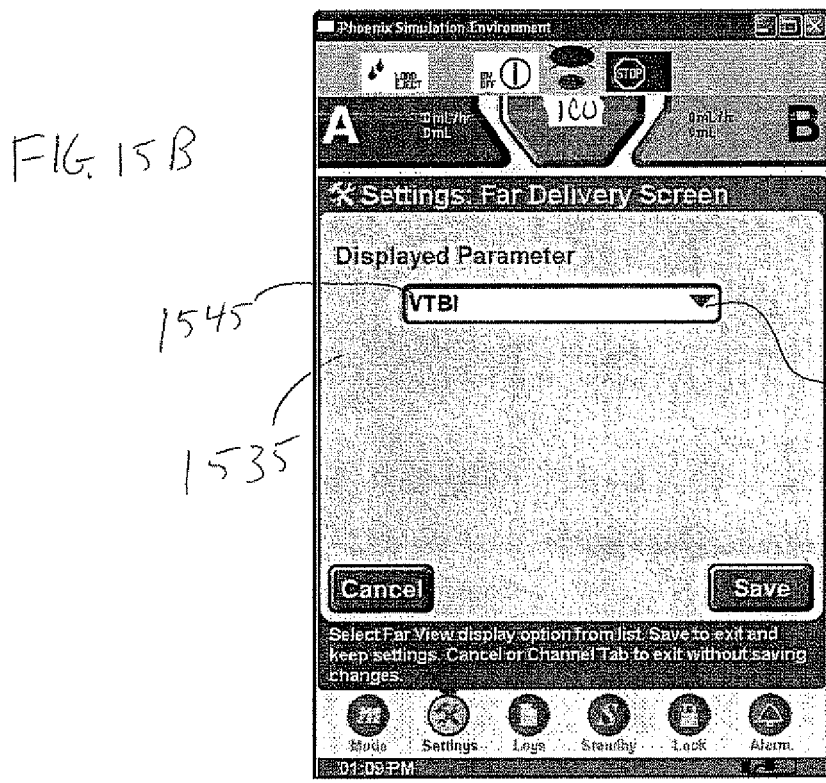
Figure 15C:
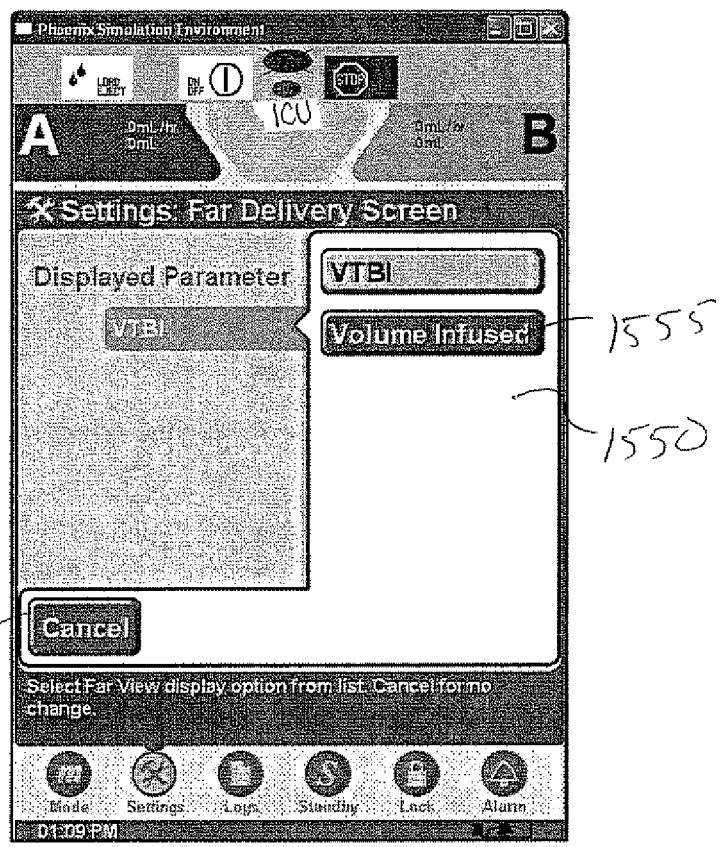
Figure 16:
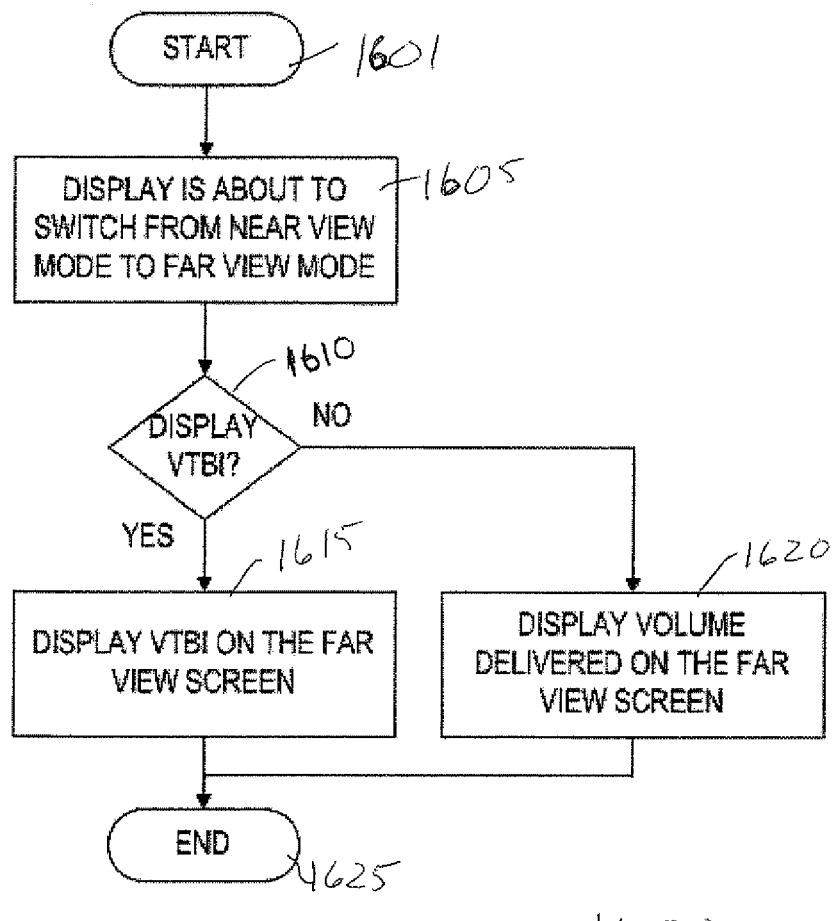
FIG. 16 is a flow chart for a program for determining a display parameter, in accordance with the present invention.

With reference to FIGS. 14 to 16, in another aspect of the present invention, the drug library, located within the medication management system and downloaded to the medical device, can be configured to display either the VTBI or the volume infused as a default setting on the far view delivery screen. In another or the same embodiment, the user can change the default setting at the medical device, as provided in more detail below.

With reference to FIG. 14, illustrated is a screen shot of a graphical user interface 1400 for changing a plurality of settings of a drug library for a chosen CCA. In this example, the CCA is the Intensive Care Unit (ICU), though it should be understood that device settings for other CCAs may be similarly configured. The drug library includes drug and device related information, which may include but is not limited to drug name, drug class, drug concentration, drug amount, drug units, diluent amount, diluent units, dosing units, delivery dose or rate, medication parameters or limits, device/infuser settings and/or modes, CCA designations and constraints, and library version. Through the maintain drug library program 42 the drug library may be configured to provide a medical device 14 that includes a customized display. In one embodiment, the display is customized based on the Clinical Care Area (CCA) the medical device 14 is located in, assigned to, and/or to be assigned to.

Once the drug library graphical user interface 1400 for the chosen CCA is displayed, the administrator sets the "default far view setting" 1405 to either VTBI 1410 or volume infused 1415. FIG. 14 shows that VTBI 1410 has been selected as the default far view setting 1405.

With reference to FIGS. 15A to 15C, a user of a medical device having a default far view setting 1405 can change the default setting. To change the default far view setting 1405, the user presses settings button 1525 to access the settings screen 1522. Next, the user presses the far delivery screen button 1530 to access the settings far delivery screen interface 1535 illustrated in FIG. 15B. In this illustration, the default setting was set to display VTBI 1545. To change the default to display "volume infused" the user accesses pull down menu 1550 (FIG. 15C) by activating arrow 1540. Pressing the Volume Infused button 1555 will change the default setting to display the volume infused instead of the VTBI. The user can press the save button (FIG. 15B) or the cancel button 1560 (FIG. 15C) for no change to the default setting.

With reference to FIG. 16, illustrated is a flow chart of a program 1600 for determining at the medical device whether the VTBI should be displayed or the volume infused should be displayed, as described above. Program 1600 begins at block 1601 and proceeds to block 1605 where the display is about to switch from the near view to the far view. Prior to the switch program 1600 determines the display parameter based on the default far view setting 1405 from the drug library for the CCA chosen by the user or the most recent setting established by the user at the device. Based on the current display parameter setting, program 1600 determines at block 1610 whether to display the VTBI. If yes, program 1600 proceeds to 1615 to display VTBI on the far view screen. If no, program 1600 moves to block 1620 to display the volume delivered on the far view screen. Program 1600 ends at 1625. In another embodiment, the near view screen display parameter settings could be similarly configured and/or adjusted.

Figure 6A:
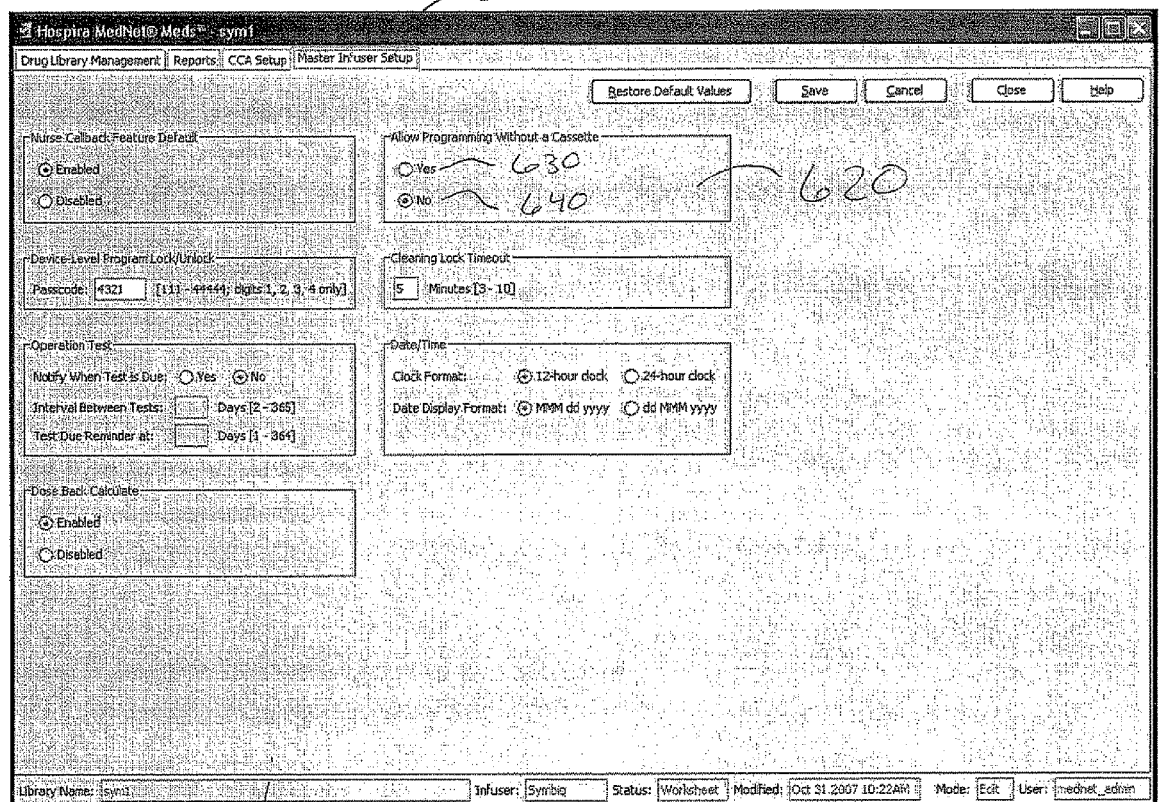
FIGS. 6A and 6B are screen shots of a graphical user interface for configuring a drug library parameter, in accordance with the present invention.
Figure 6B:
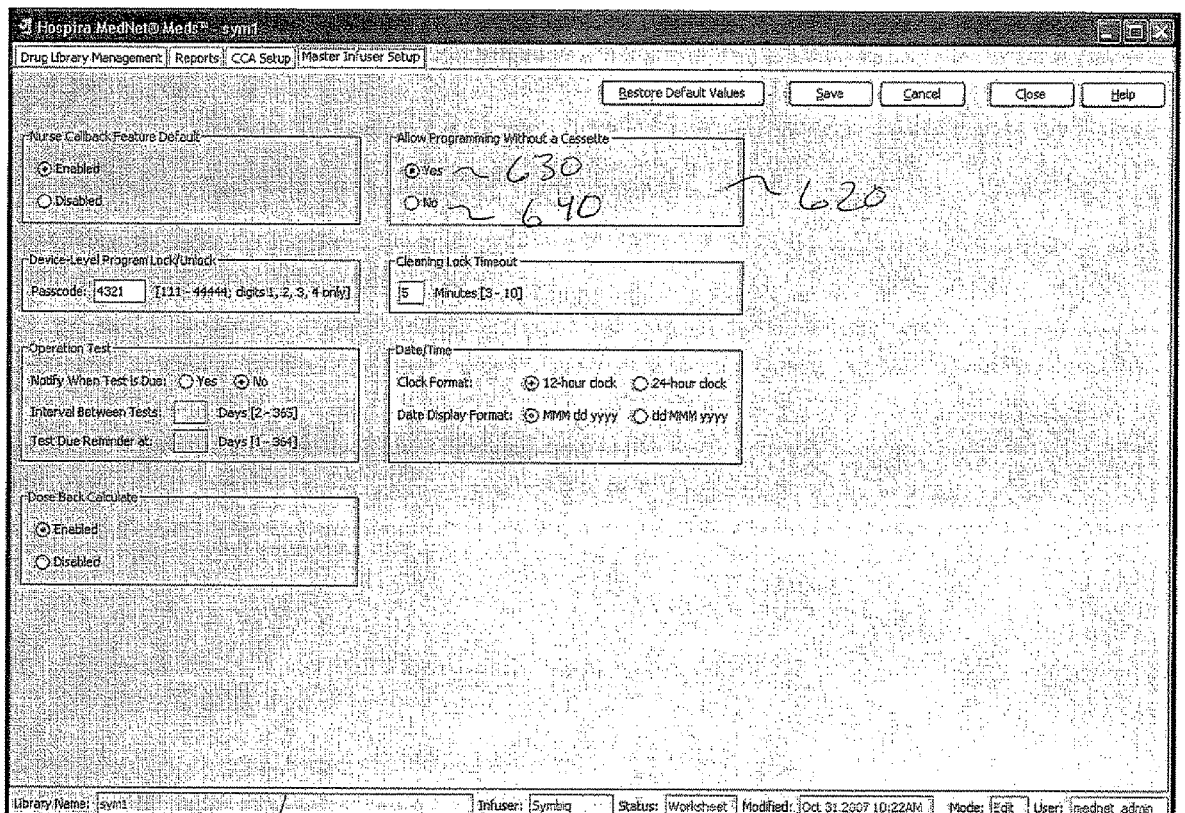

With reference to FIGS. 5, 6A and 6B, illustrated is graphical user interface 600 of an input device 38 within MMU 12 that is used to configure, within a medication management system all of the associated medical devices 14 as a part of the master infuser setup 610. Pursuant to the present invention, graphical user interface 600 is used by authorized personnel to configure medical device programming parameters. Infusion devices such as the pump 14 require an administration set to perform the infusion. In one embodiment, the administration set is a cassette. The below discussion is in relation to a cassette, however, other types of administration sets as known in the art may be used in accordance with the present invention. Prior art devices require that the cassette be in place prior to programming the pump for an infusion. There are some circumstances within the hospital environment, however, where this requirement is inefficient and wasteful of expensive supplies that go unused, merely because the clinical caregiver has set up an infusion just in case it is need in, for example, the OR, ER or the ICU. In other situations, the time it takes to program a pump only when it is needed may be harmful to the patient, especially in the OR and the emergency room. Conversely, disallowing the programming of a medical device without a cassette may enhance patient safety by, for example, reducing the risk of line confusion during setup.

Figure 7A:
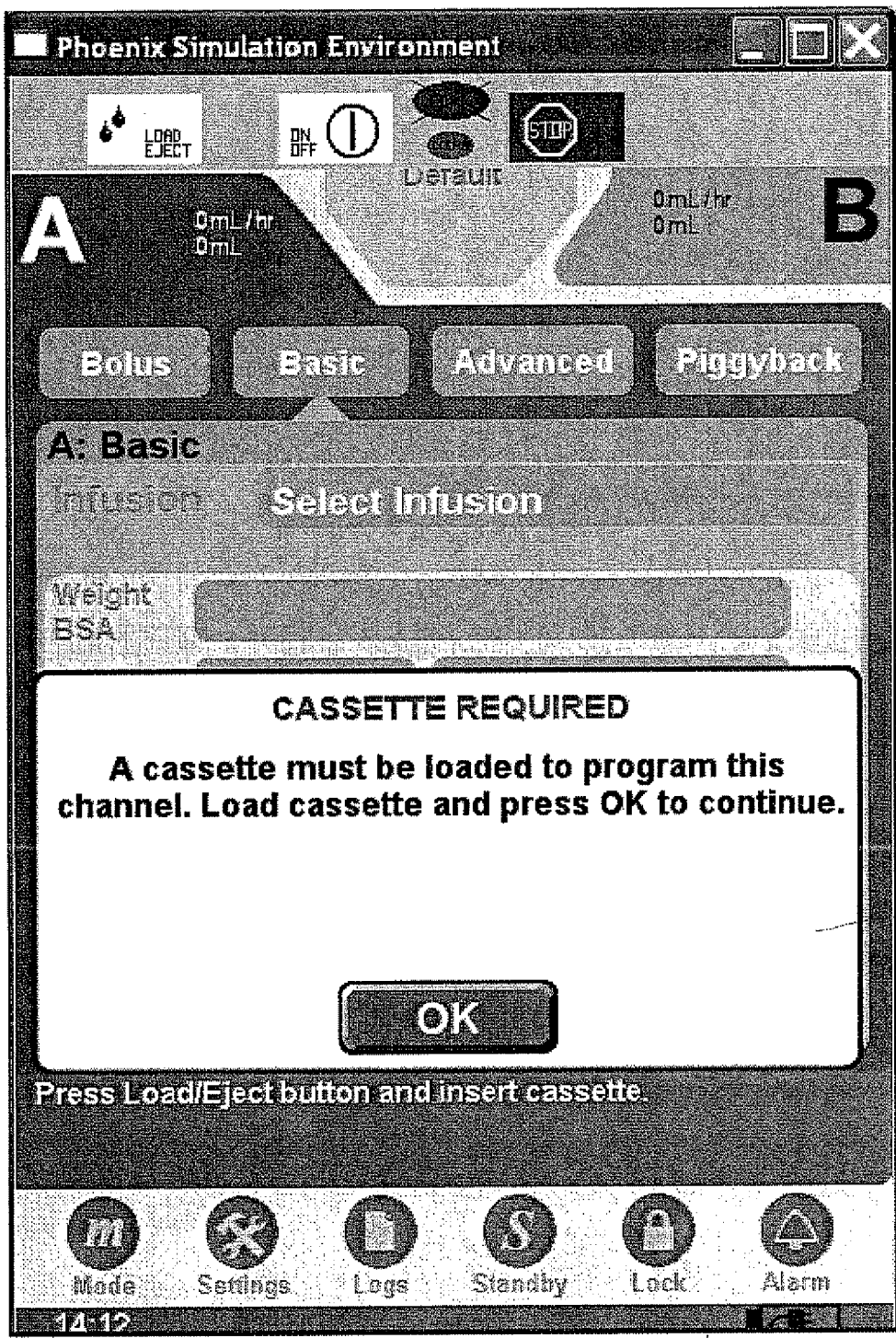
FIGS. 7A and 7B are screen shots of a graphical user interface for configuring medical device specific parameters, in accordance with the present invention.
Figure 7B:

Therefore, in one aspect of the present invention, the drug library, via the master infuser setup 610, can be configured by a hospital administrator based on hospital policy and procedure. FIGS. 6A and 6B illustrate the configurable parameter 620 of allowing programming of infusion pumps with or without a cassette in place. Thus, at graphical user interface 600, an administrator may choose to allow programming without a cassette by selecting "yes" 630 (FIG. 6B) or disallow programming without a cassette by selecting "no" 640 (FIG. 6A). FIG. 7A illustrates a warning message 720 that appears on screen 700 when a user tries to program the medical device without a required cassette. Once the cassette is loaded, the programming can continue. FIG. 7B illustrates how a programming screen would appear if the programming was started with a cassette in place, whether or not required, or if programming was started without a cassette which has been allowed by the configuration of the master infuser setup 610.

Figure 8:
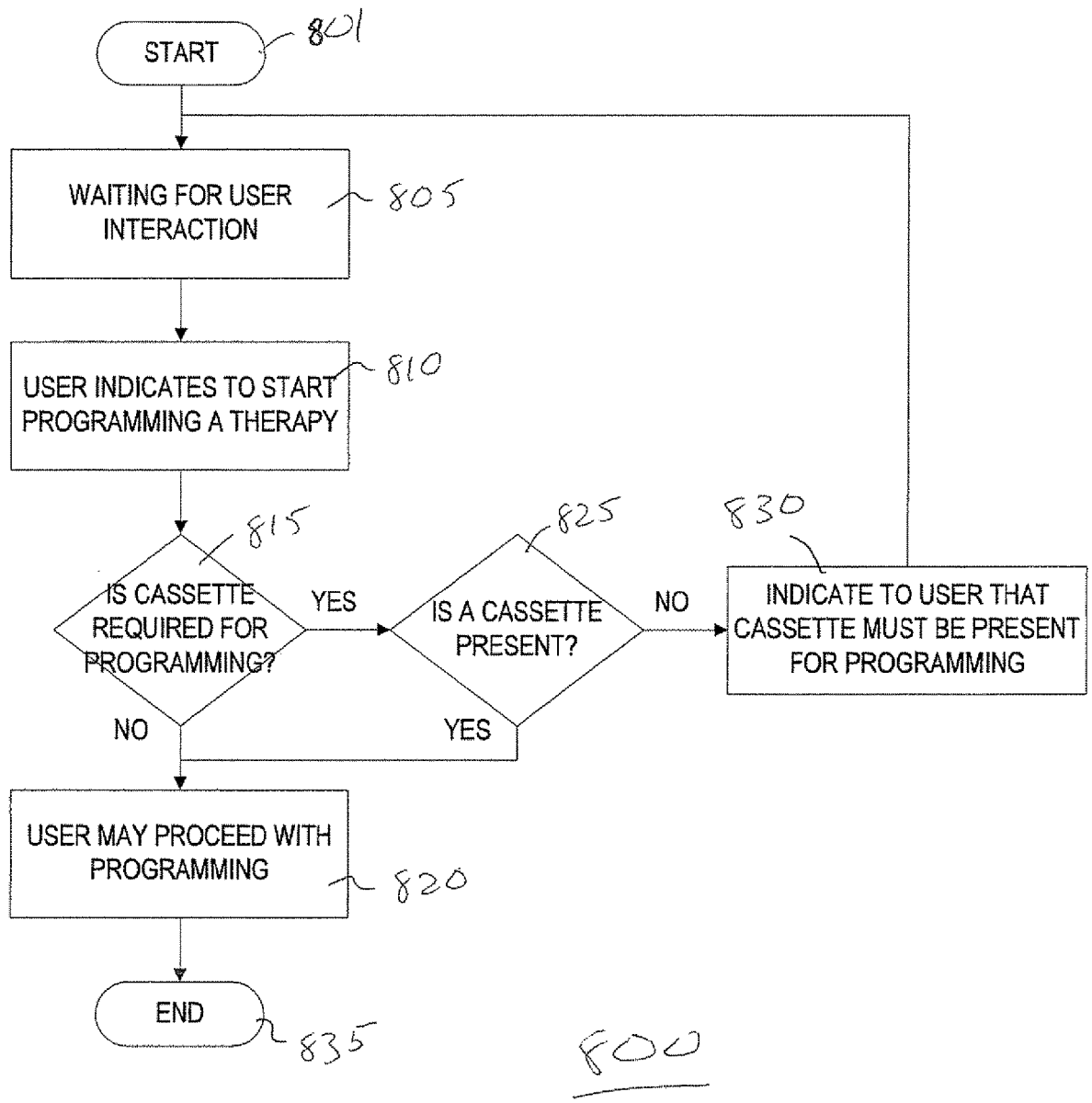
FIG. 8 is a flow chart for a program for allowing or disallowing programming of a medical device in regards to the presence of a cassette, in accordance with the present invention.

With reference to FIG. 8, a flow chart of a program 800 for determining at the medical device whether the drug library within the memory of the medical device allows the medical device to be programmed with or without a cassette in place. Program 800 begins at 801 and proceeds to 805 where upon some user interaction (e.g. power on), program 800 proceeds to block 810 where the program 800 receives an indication that the user is starting to program a therapy. Upon receiving the indication, program 800 determines at block 815 whether a cassette is required for programming. If no, the program allows the user to proceed, block 820 and the program ends at block 835. However, if at block 815 it is determined that a cassette is required, program 800 determines at block 825 whether a cassette is in place. If yes, program 800 proceeds to block 820 to allow the user to continue and the program ends at 835. If, at block 825, program 800 determines that a cassette is not present, a warning message 720 is displayed that indicates to the user that a cassette is required. The user may either place a cassette as required and continue or discontinue the attempted programming.

Another aspect of the present invention allows the user to modify the CCA without the interruption of a current infusion. FIGS. 9A to 11 illustrate various embodiments of allowing the user to modify the CCA "on the fly." The ability to change the CCA is this manner increases user and workflow efficiency. In particular, the ability to change the CCA while an infusion is running is crucial where a patient is being transported from one CCA to another such as from the emergency room (ER) to the OR, or from the OR to the ICU. This ability to change the CCA also enhances patient safety where time to wait for an infusion to end may be harmful to the patient. FIGS. 9A to 9G illustrate a series of screen shots of a medical device configured to allow the CCA to be changed while an infusion is ongoing on another channel of the multi-channel pump.

Figure 9A:
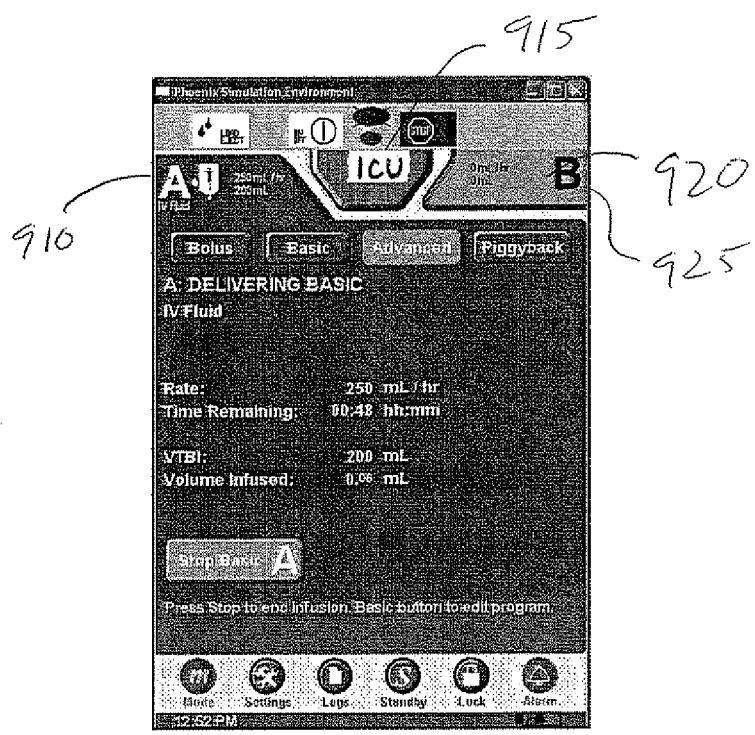
FIGS. 9A to 9G are screen shots of a graphical user interface, illustrating changing a clinical care area, in accordance with the present invention.
Figure 9B:
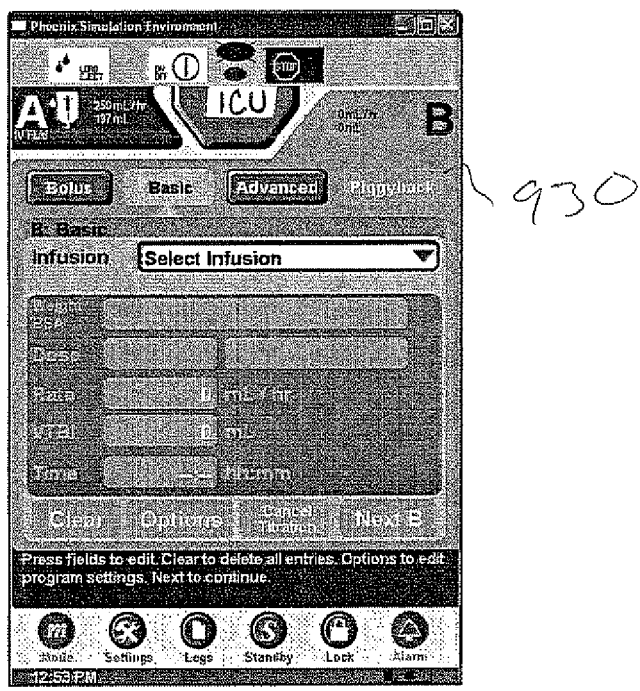
Figure 9C:
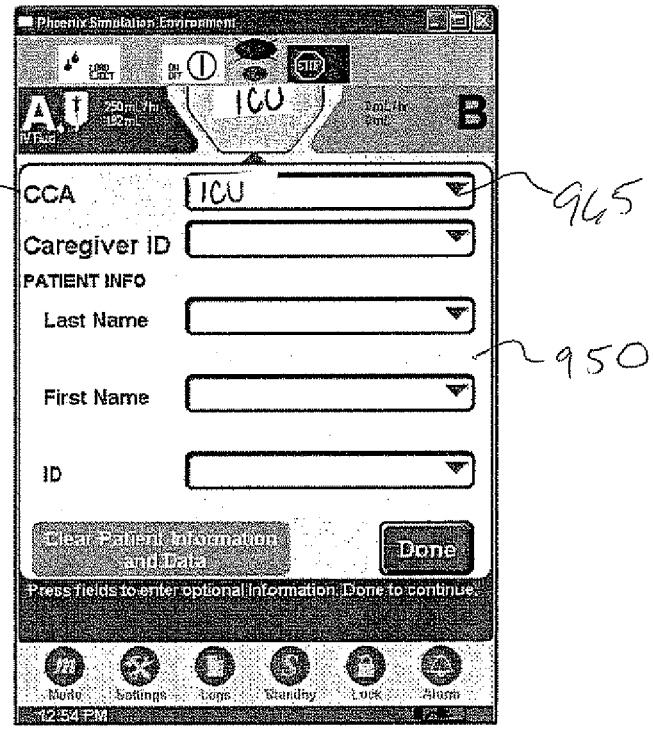
Figure 9D:
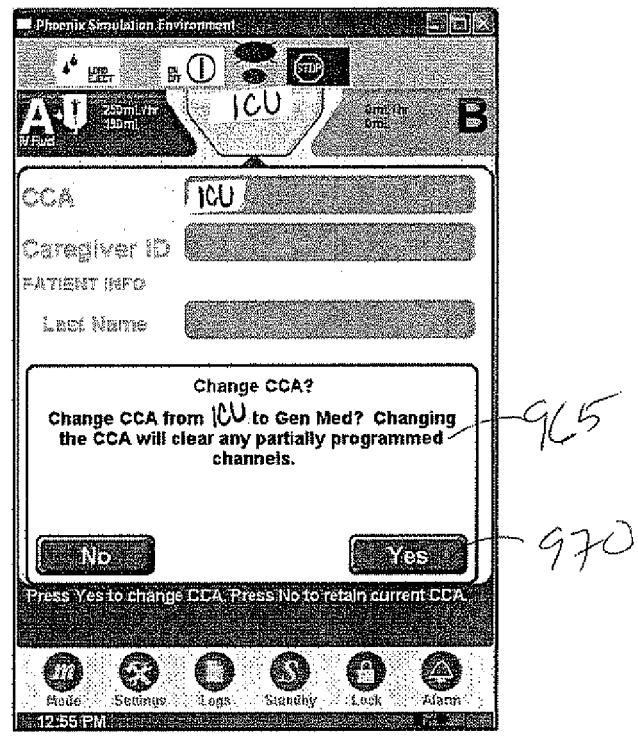
Figure 9E:
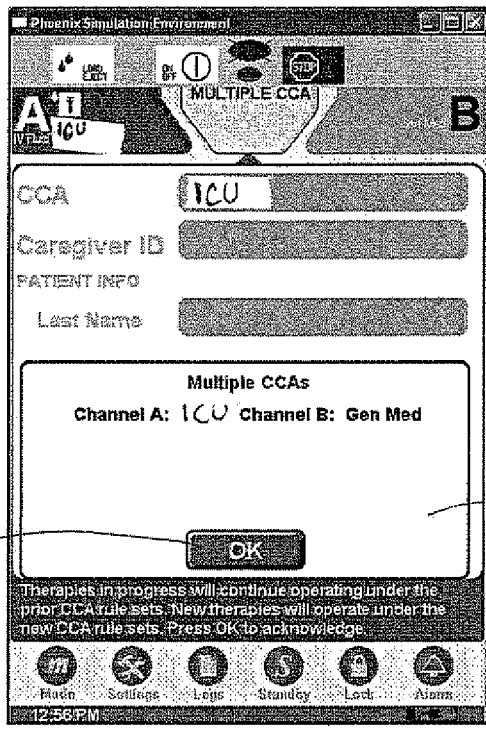
Figure 9F:
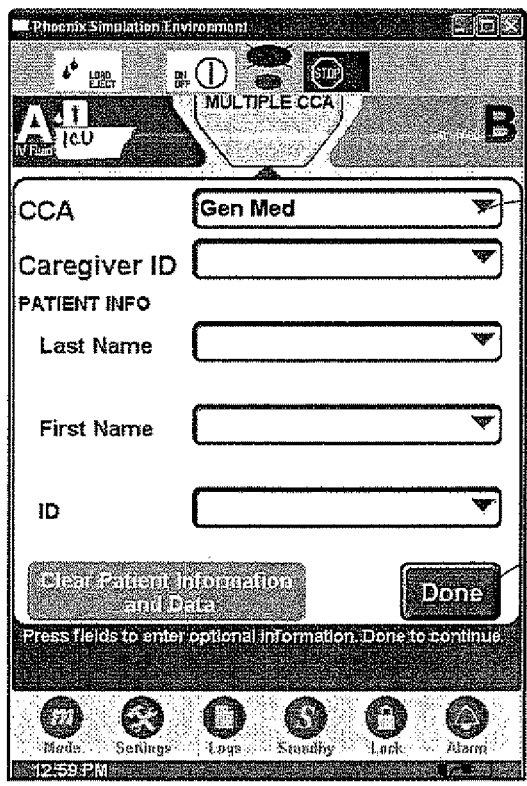
Figure 9G:
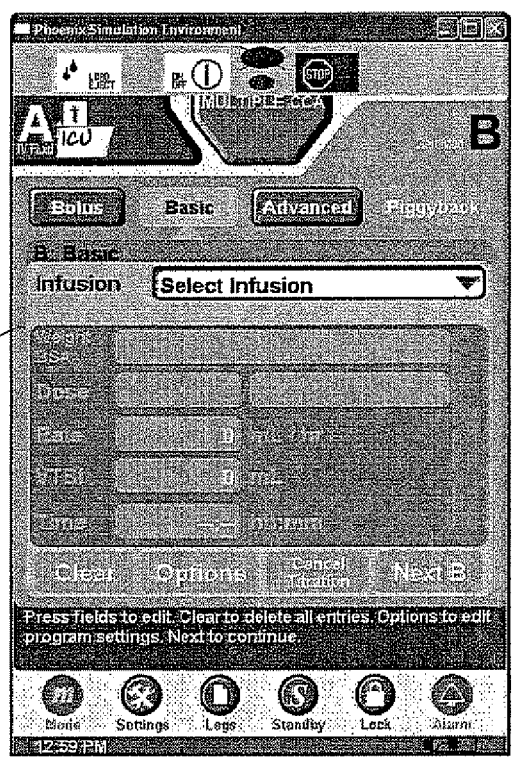

FIG. 9A illustrates that a therapy is delivering on channel A 910 with the ICU CCA 915. In this example, a user wants to change the CCA and program Channel B 920. The user selects channel B by pressing tab B 925, which brings up the channel B programming display screen 930 shown in FIG. 9B. Moving from FIG. 9B to FIG. 9C, the patient information button 940 has been pressed. Pressing the patient information button displays a patient information data field 950 for entry of patient data and changing the CCA 960. When the user presses the CCA button, a "Change CCA" message 965 appears requesting that the user confirm that the CCA is to be changed (FIG. 9D). In this example, the user wants to change the CCA from ICU to Gen Med. To confirm, the user presses the "yes" button 970. In response to the confirmation, a "multiple CCAs" system message 975 appears. To confirm, the user presses the "OK" button 980. Once the OK button 980 has been pressed, the CCA has been changed at 985 and a "Done" button 990 is displayed to continue with the programming of the infusion at infusion screen 995 (FIG. 9G).

Figure 10:
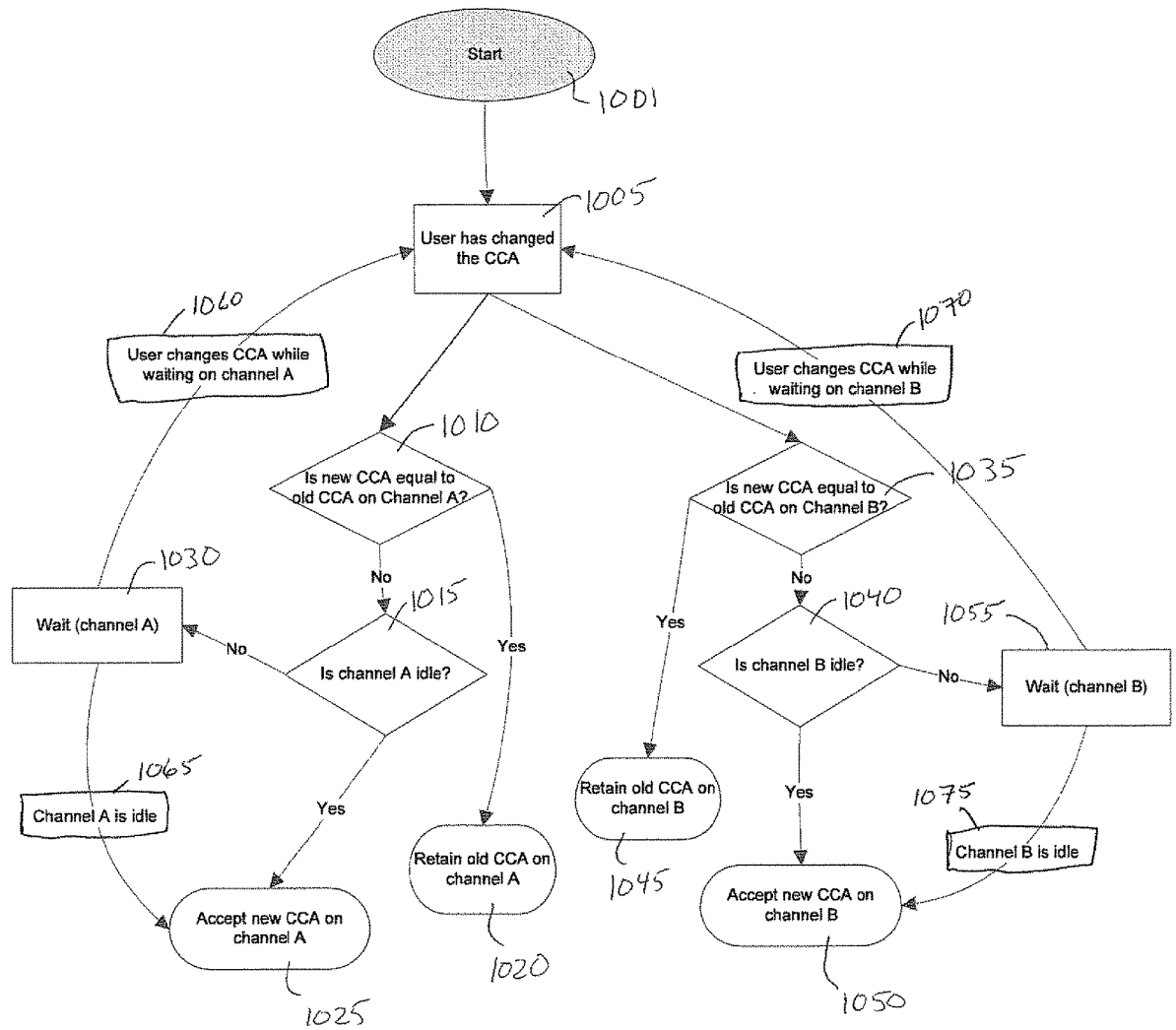
FIG. 10 is a flow chart for a program for changing a clinical care area in a multi-channel infusion pump, in accordance with the present invention.

With reference to FIG. 10, illustrated is a program 1000 for changing the CCA at a multi-channel medical device 14. Program 1000 starts at 1001 and proceeds to block 1005 where it is determined that the user has changed the CCA. Program 1000 then determines at block 1010 whether the new CCA is the same as the old CCA for Channel A If yes, the program proceeds to block 1020 to retain the old CCA on Channel A If no, program 1000 proceeds to block 1015 to determine whether channel A is idle. If yes, program accepts the new CCA on channel A at block 1025. If no, channel A is set to wait at block 1030 until either 1) the user changes the CCA while waiting on channel A (block 1060), whereby program 1000 proceeds to 1005; or 2) channel A becomes idle (block 1065), whereby program 1000 proceeds to block 1025 and accepts the new CCA on channel A Additionally, when a user has changed a CCA (block 1005), channel B is evaluated. Program 1000 proceeds from block 1005 to block 1035 to determined whether the new CCA is the same as the old CCA for Channel B. If yes, the program proceeds to block 1045 to retain the old CCA on Channel B. If no, program 1000 proceeds to block 1040 to determine whether channel B is idle. If yes, program 1000 accepts new CCA on channel B, block 1050. If no, channel B is set to wait at block 1055 until either 1) the user changes the CCA while waiting for channel B (block 1070), whereby program 1000 proceeds to 1005; or 2) channel B becomes idle (block 1075), whereby program 1000 proceeds to block 1050 and accepts the new CCA on channel B.

Figure 11:
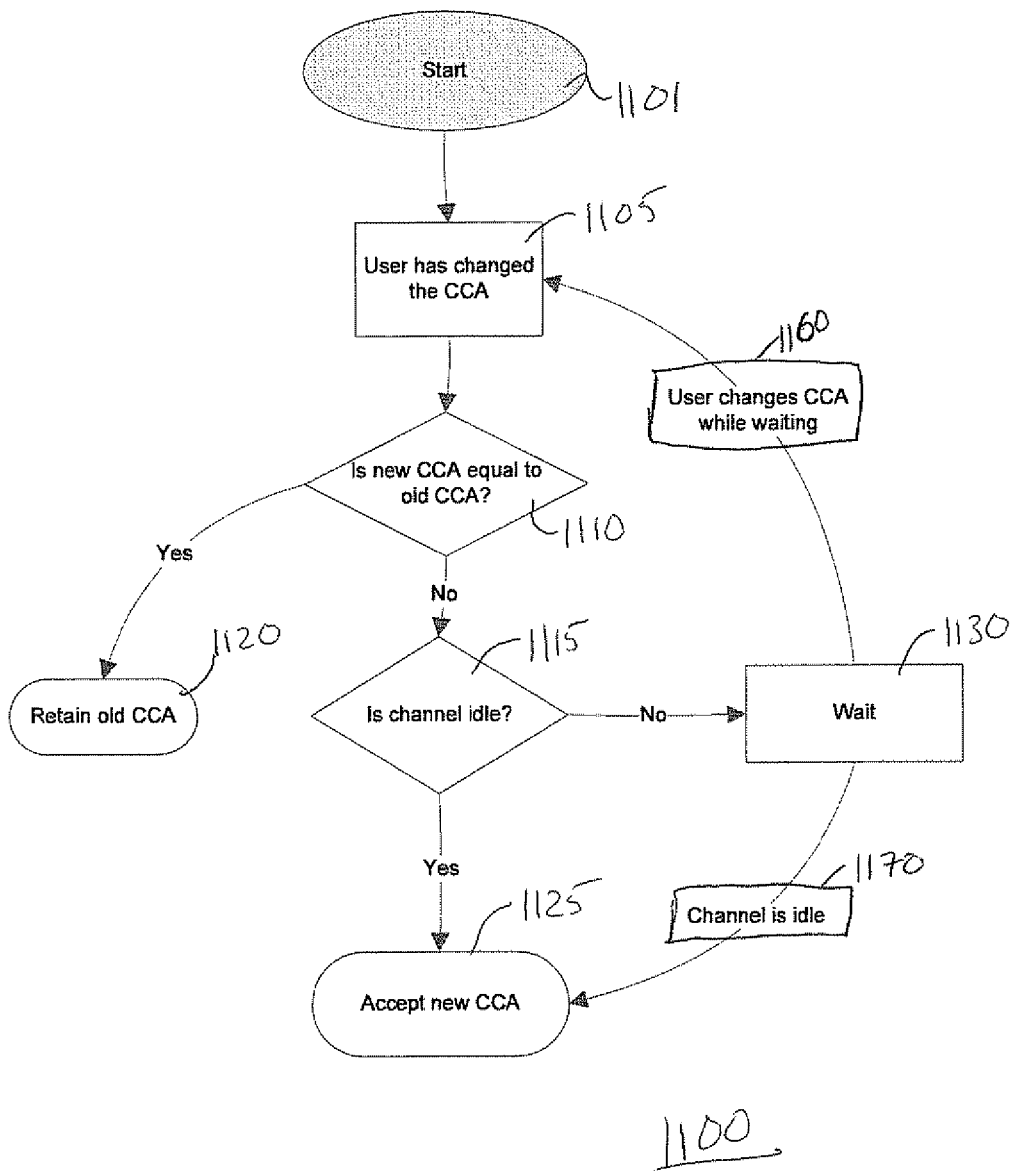
FIG. 11 is a flow chart for a program for changing a clinical care area in a single channel infusion pump, in accordance with the present invention.

With reference to FIG. 11, illustrated is a program 1100 for changing the CCA at a single channel medical device. Program 1100 starts at 1101 and proceeds to block 1105 where it is determined that the user has changed the CCA. Program 1100 then determined at block 1110 whether the new CCA is the same as the old CCA. If yes, the program proceeds to block 1120 to retain the old CCA. If no, program 1100 proceeds to block 1115 to determine whether the channel is idle. If yes, program 1100 accepts the new CCA, block 1125. If no, the channel is set to wait at block 1130 until either 1) the user changes the CCA while waiting (block 1160), whereby program 1100 proceeds to 1105; or 2) the channel becomes idle (block 1170), whereby program 1100 proceeds to block 1125 and accepts the new CCA.

Figure 12A:
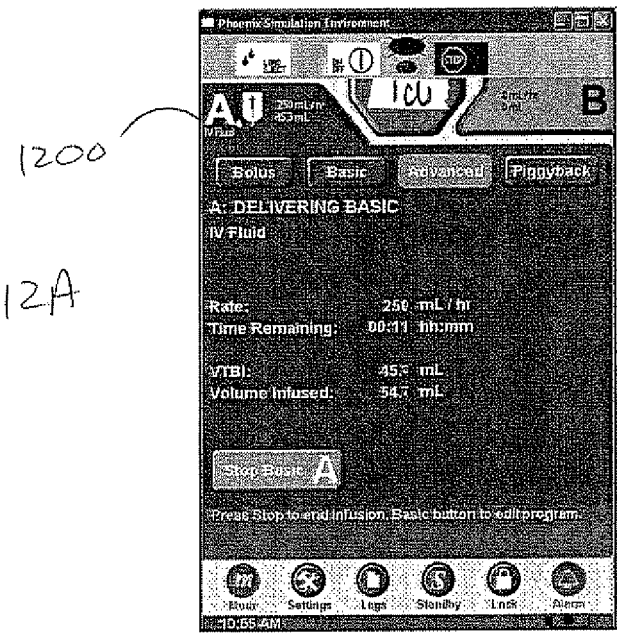
FIGS. 12A to 12F are screen shots of a graphical user interface, illustrating programming of additional VTBI to current infusion, in accordance with the present invention.
Figure 12B:
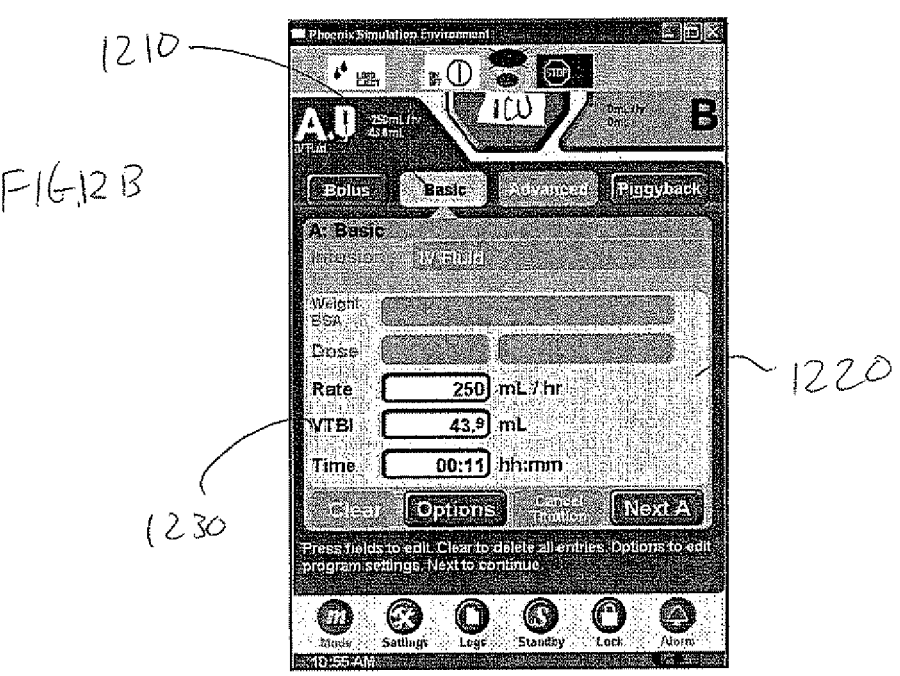
Figure 12C:
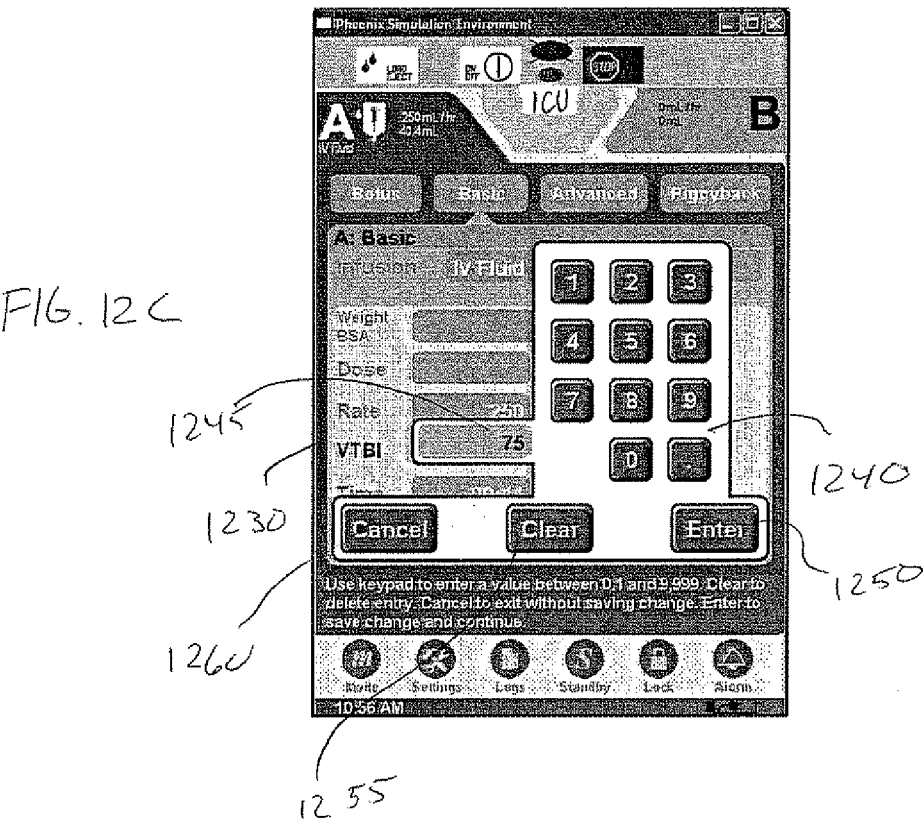
Figure 12D:
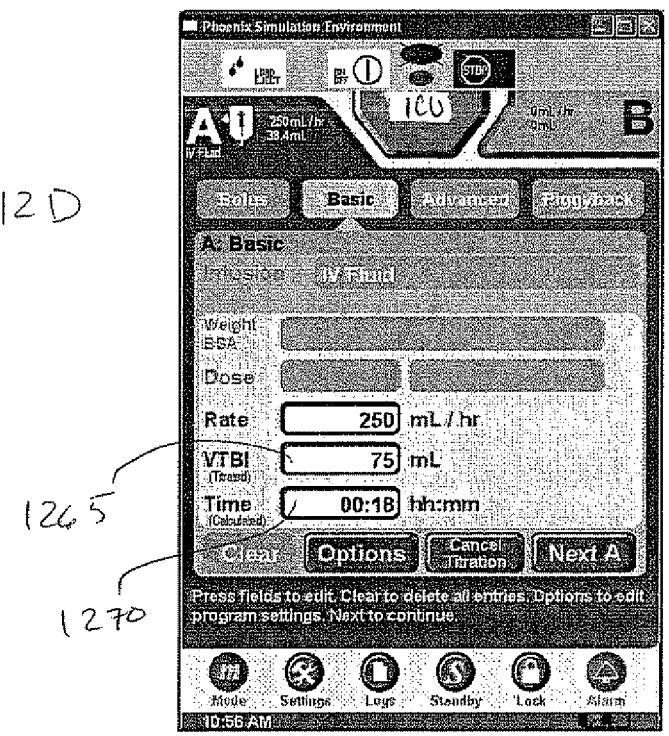
Figure 12E:
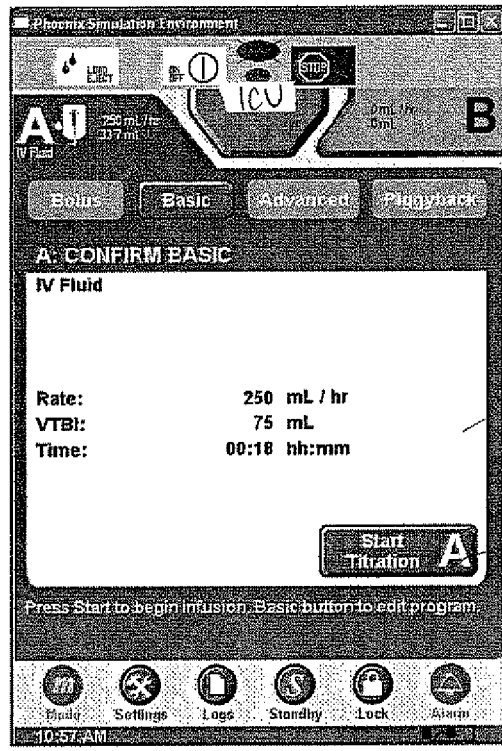
Figure 12F:
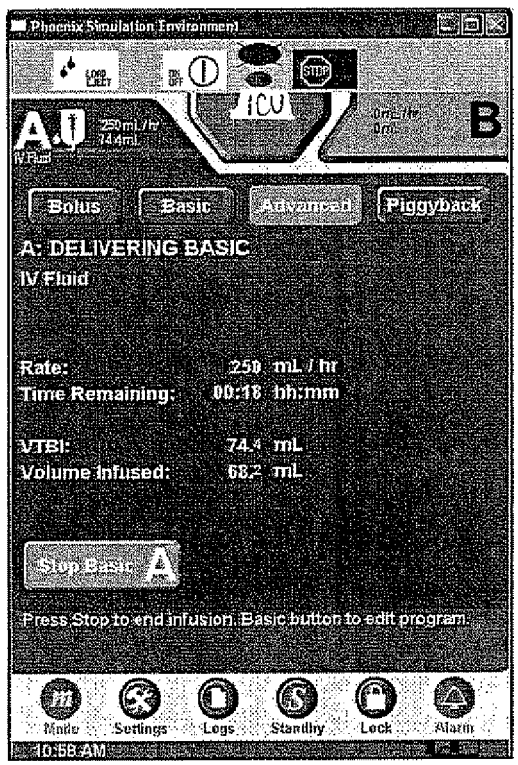
Figure 13:
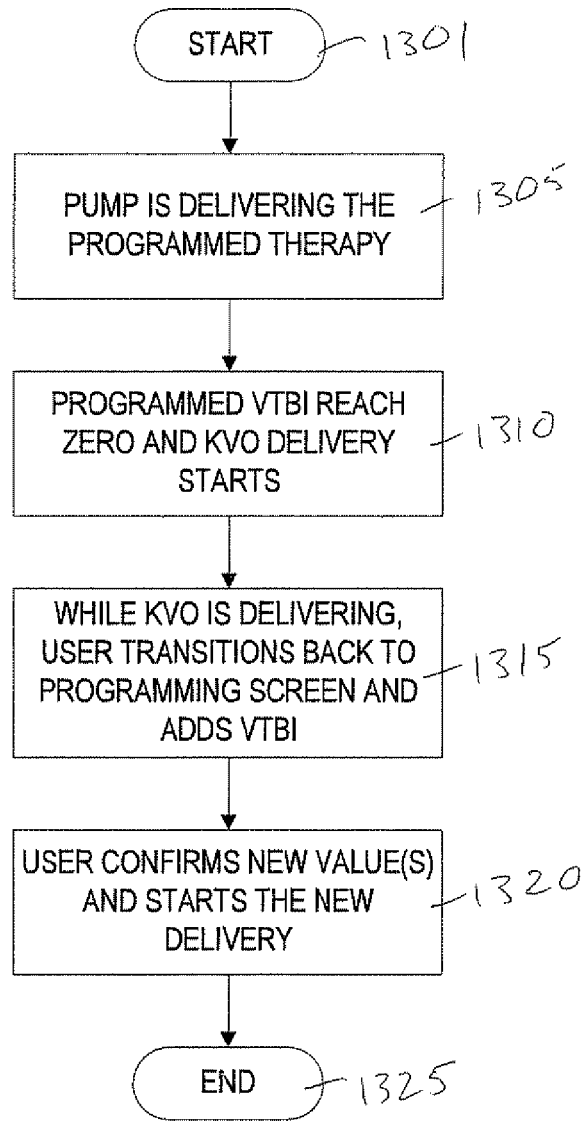
FIG. 13 is a flow chart for a program for adding additional VTBI to a current infusion, in accordance with the present invention.

With reference to FIGS. 12A to 13, illustrated is another aspect of the present invention that allows a medical device 14 user to modify the VTBI parameter to specify additional fluid when an infusion is nearing completion or is delivering in a KVO (keep vein open) mode. A configured medical device that includes a program to allow the additional fluid provides for more efficient workflow as well as a more efficient user. In one embodiment of the invention, the program for allowing additional VTBI maintains all other delivery parameters while allowing the user to specify the additional VTBI. Thus, the user does not have to re-enter common delivery parameters when only an additional VTBI is needed. This reduces programming effort, saves time and reduces the potential for errors.

FIGS. 12A to 12F illustrate, using a series of screen shots, one embodiment of a program for modifying the VTBI delivery parameter. At FIG. 12A, a basic infusion is delivering on channel A, as shown by screen display 1200. At this point in the infusion, FIG. 12A shows that the remaining VTBI is 45.3 ml. FIG. 12B illustrates that the user has pressed "basic" button 1210. A data entry field 1220 appears based on the pressing of the basic button 1210. At data entry field 1220, the user can press the particular field to edit. FIG. 12C illustrates that the user pressed the VTBI button 1230 to edit the VTBI. In response to pressing the VTBI button 1230 a keypad 1240 appears on the display screen. Here, the user enters the total amount of VTBI desired. In this exam pie, the user enters 7 5 via the keypad 1240 into the data field for VTBI 1245. The user then presses "Enter" 1250 to save the changes and continue. Alternatively, the user can press "Clear" 1255 to delete the entry or cancel 1260 to exit without saving the changes. FIG. 12D illustrates that the VTBI has been changed to 75 ml and entered. FIG. 12D also illustrates that the time remaining has been recalculated and is displayed in area 1270 based on the new VTBI displayed in area 1265. At FIG. 12E, a confirmation of titration screen 1275 has appeared to confirm the new VTBI. The user confirms the change to the VTBI by pressing "Start Titration" button 1280. FIG. 12F illustrates that the infusion has been updated with the new VTBI and is continuing to run. In one embodiment, the method illustrated in FIGS. 12A to 12F is used to add to the VTBI the fluid remaining in the fluid container that is currently infusing. In another embodiment, the user may add a new container of fluid as long as all other delivery parameters remain the same as the currently running infusion.

FIG. 13 is a flow diagram illustrating one embodiment of a method 1300 for adding additional VTBI to a current infusion. Method 1300 starts at block 1301 and proceeds to block 1305 where it is determined that the pump is delivering a programmed therapy. Method 1300 continues at block 1310 where the programmed VTBI reached zero and the KVO delivery starts. At block 1315, a user accesses a VTBI programming screen 1220 and enters a VTBI value 1245. The user confirms the new value at block 1320 and starts the new delivery. Method 1300 ends at 1325. One skilled in the art will appreciate from the disclosure herein that such adding of VTBI can also be adapted for use in bolus or piggyback situations.

Figure 21A:
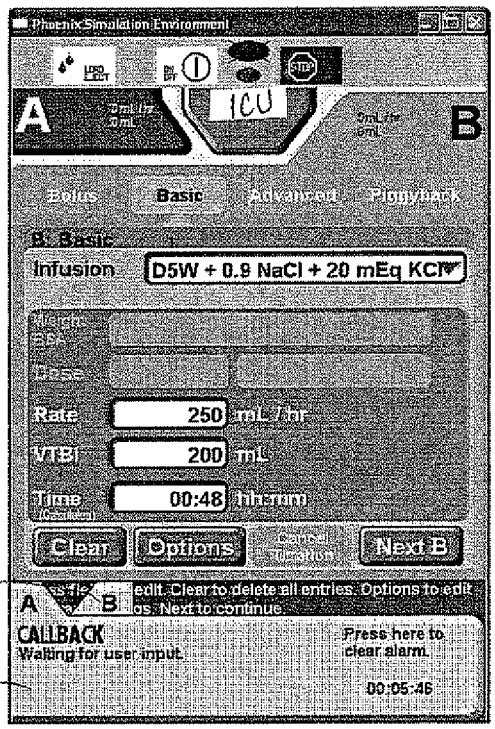
FIGS. 21A and 21B are screen shots of various graphical user interface call back alarms, in accordance with the present invention.

With reference to FIGS. 21A to 22, one embodiment of the present invention provides for improved callback rules for the medical device. Medical devices generally have three classes of callback alarms based on urgency: High Urgency (e.g. Air-In-Line); Medium Urgency (e.g. Inactivity callback); and Low Urgency (e.g. Battery not Charging). In one embodiment of the invention, the alarms are configured at the drug library. In one embodiment, the alarms are configured at the drug library based on the CCA in which the medical device resides. In another embodiment, the alarms are configured at the drug library master infuser settings so that the alarm configurations apply to all medical devices within the medication management system. In other embodiments, the alarms are configurable by the clinician at the medical device. For example, in one embodiment, default alarm settings were configured at the drug library, and sent to the medical device where, depending on the alarm configuration rules set by the hospital administration, a clinician may modify the alarm based on factors such as the particular CCA, or personal preference.

In one embodiment of the invention, a specific alarm type or configuration is assigned to each class of urgency such that a clinician can determine the urgency of the callback alarm upon hearing the alarm. In one embodiment of the invention, each class of alarm is assigned a different melody, a different tone or series of tones and/or a different volume. In other embodiments, the frequency of the alarm is configured based on the class of alarm. In other embodiments, the volume, melody, tone and/or frequency may escalate based on a non-response by the clinician.

In one embodiment of the invention, when an audible alarm occurs at the medical device, the audio volume starts at the volume setting configured at the drug library and or by the clinician. However, if the alarm is not acknowledged, the volume is automatically escalated to a predetermined volume after a predetermined time out period passes. In one embodiment, the time out period is configurable at the drug library. In another embodiment, the time out period is configurable at the drug library for each particular CCA. In yet another embodiment, the time out period is configurable at the medical device. In another embodiment, a default value for the time out period is set at the drug library and may be changed at the medical device to a value that does not exceed the default value. For example, if the default time out period is 20 seconds, the user may set the time out period to less than 20 seconds such as for 10 seconds. In on embodiment of the invention, the volume escalates for only those alarms in the High Urgency class of alarms. In other embodiments, the volume escalates for both High Urgency and Medium Urgency classes of alarms.

In another embodiment of the present invention, the alarm tone escalates after a predetermined time out period if the alarm is not acted upon. In this embodiment, a default tone set at the drug library may be configurable by a user at the medical device. In one embodiment, the pitch of the tone becomes higher when the alarm escalates due to the non-response of the clinician.

In another embodiment of the present invention, the alarm comprises a predetermined tone melody. In one embodiment, a different tone melody is chosen for each class of alarm urgency or priority. In one embodiment, the High Urgency audible alarm is a sequence of six or seven tones that continually repeat until the alarm is acted upon by the clinician. In one embodiment, a brief pause of the tone sequence (melody) occurs between each repeat of the sequence. In one embodiment, the melody for the High Urgency alarm also escalates in volume with continued inactivity by the clinician. In one embodiment, the volume of the melody escalates after a predetermined length of time. In one embodiment, the escalation of volume is configured at the drug library. In another embodiment, the volume escalation is set as a default in the drug library and is further configurable at the medical device by the clinician.

In another or the same embodiment, the Medium Urgency audible alarm is a sequence of three tones. In one embodiment, the tone sequence (melody) repeats after a predetermined length of time if the clinician has not responded to the alarm. In one embodiment the predetermined length of time is 1 to 2 minutes. In another embodiment, the predetermined length of time is from 1 to 60 seconds. In one embodiment, the predetermined length of time is configured at the drug library. In another embodiment, the predetermined length of time is set as a default at the drug library and is further configurable by the clinician at the medical device.

In another embodiment, the Low Urgency audible alarm is a sequence of two tones. In one embodiment, the tone sequence repeats every two to ten minutes until acted upon by the clinician. The time to repeat may be configured as above for the Medium Urgency alarm.

In one embodiment, the High Urgency alarms are configured to have a melody with a very fast paced tempo. While the lesser urgency alarms have a melody with a slower paced tempo. In one embodiment, an alarm comprising a melody escalates in tempo when the alarm is not responded to by the user. In one embodiment, the alarm is configurable by the user at the medical device to a melody of the user's choice. In an example, a melody may be assigned to each user whereby the user sets the alarm on each medical device the user is responsible for to that one melody. In this manner, any one user in a location with multiple users can identify by sound that the alarm is for a medical device of a patient under their specific care.

Figure 21B:
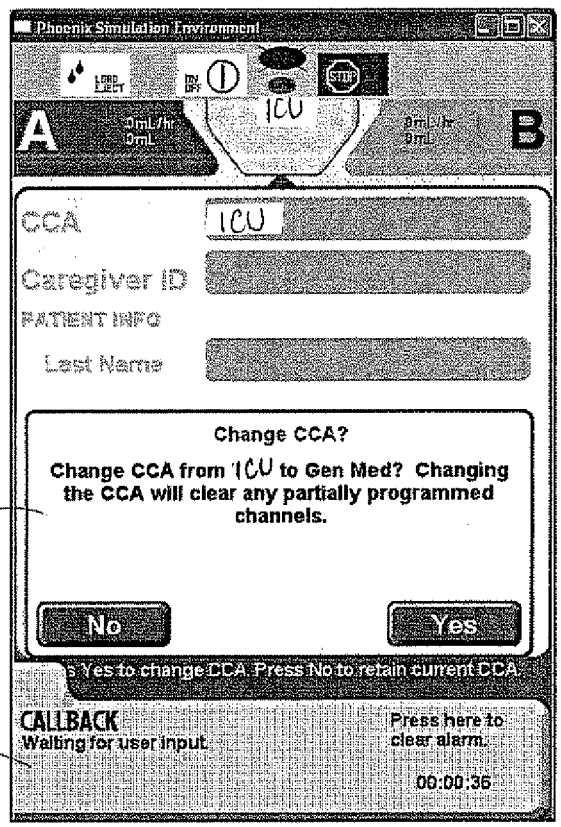

FIG. 21A illustrates a screen shot of a medical device showing that a channel level callback alarm 2110, 2115 has sounded for each channel A and B where a therapy was partially programmed and no other action was taken by the user. FIG. 21B illustrates a device level callback alarm 2120 has appeared because no keypress was made while a popup 2125 was displaying.

With regard to FIG. 22, a flow chart of a program 2200 for escalating an audible callback alarm, in accordance with the present invention. Program 2200 begins at 2201 and proceeds to block 2205 where an alarm has been activated. At block 2210, program 2200 determines whether the clinician has acknowledged the alarm during a timeout period. If yes, program 2200 proceeds to end at 2235. If no, program 2200 proceeds to block 2215 where a determination is made as to whether the current volume is at a maximum level. If no, program proceeds to block 2220 where the program increases the alarm volume. If yes at block 2215, program 2200 proceeds to block 2225 to determine whether the melody is at a High Urgency and has a melody change been configured. If yes, program 2200 proceeds to end at 2235. If no at block 2225, program 2200 proceeds to block 2230 to change the melody. Program 2200 then proceeds to end at block 2235.

When an alarm occurs on a medical device it may apply to the entire device (e.g. low battery) or it may only apply to a specific channel (e.g. inactivity callback on channel A). If the alarm is channel specific, the user needs to navigate to the channel to view what is causing the callback. In another aspect of the present invention, a device program automatically takes the user to the precise location of the alarm when the user touches the alarm display area on the display screen as will be described below with reference to FIGS. 23A to 23C.

Figure 23A:
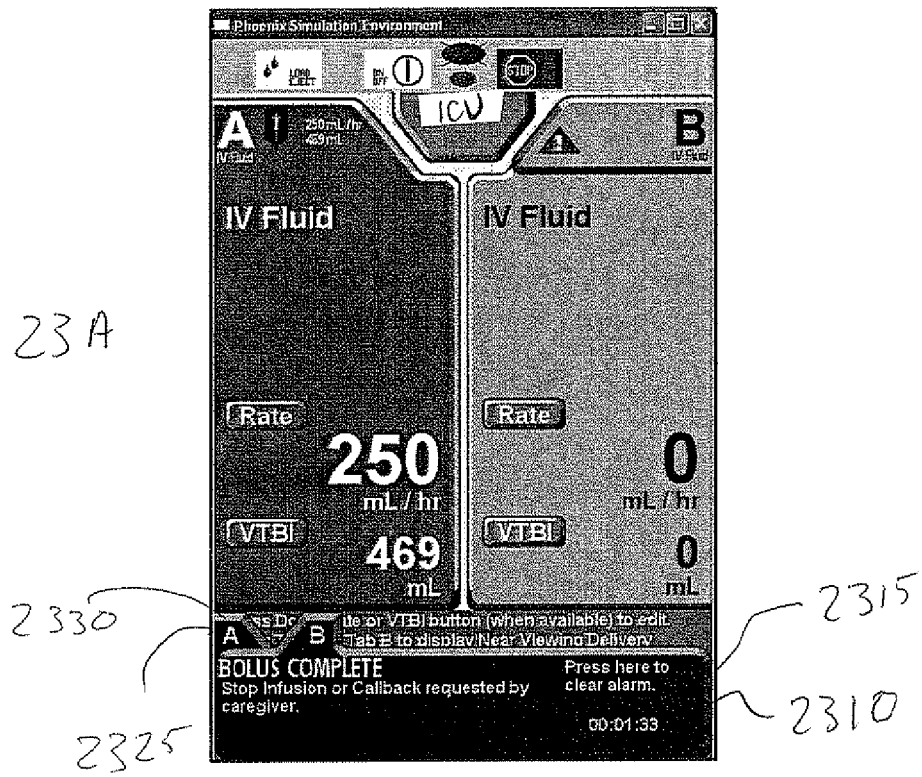
FIGS. 23A to 23C are screen shots illustrating graphical user interface alarm navigation shortcut buttons, in accordance with the present invention.
Figure 23B:
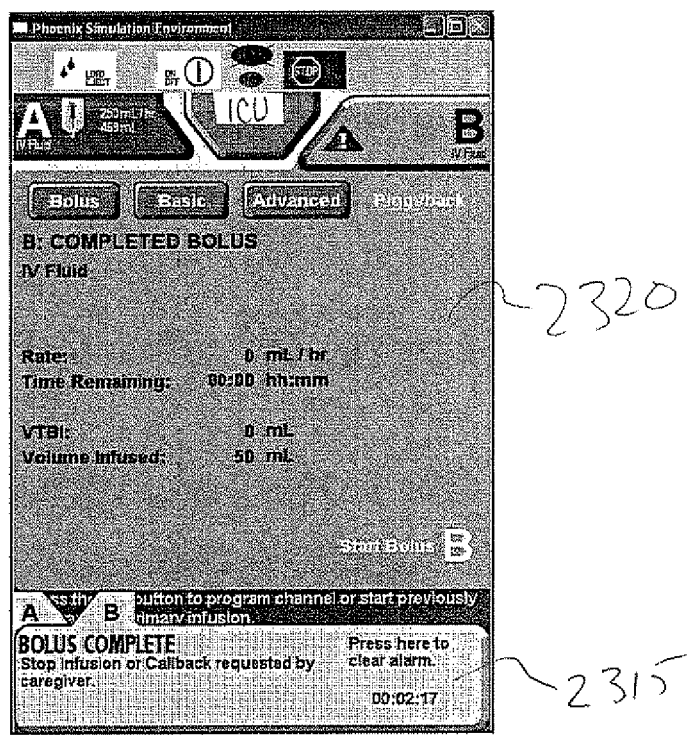
Figure 23C:
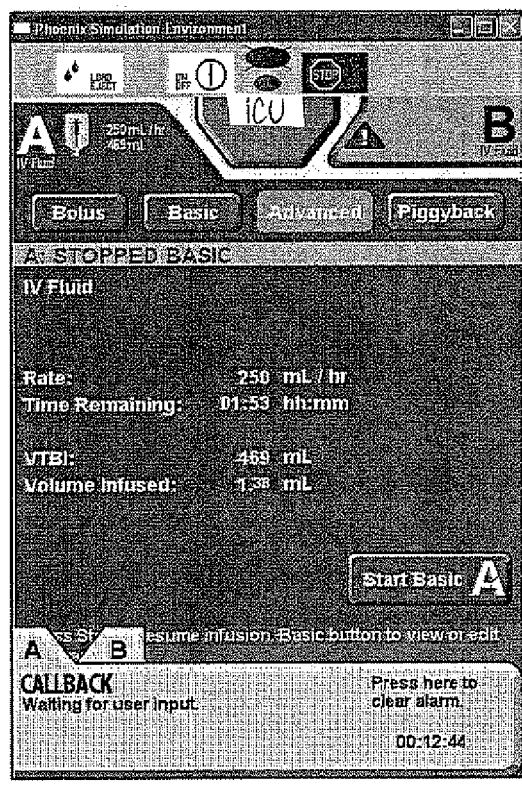

FIGS. 23A to 23C are screen shots of a display interface for a multi-channel infusion pump. In this example, the infusion pump has a therapy programmed for both channel A and channel B. Channel A is idle waiting for the bolus programmed on channel B to complete. FIG. 23A shows that an alarm 2310 has occurred on channel B based on the completion of the bolus infusion programmed on channel B. The drug library or the user had previously configured the pump to stop the infusion or request the pump generate a callback to them when the bolus was complete. When the user presses alarm tab B 2315 the user is taken directly to the display screen 2320 for channel B. Display screen for channel B indicates that the bolus is completed.

FIG. 23A also illustrates that an alarm 2325 has occurred for channel A When the user presses alarm tab A 2330, the user is taken directly to display screen 2335 shown in FIG. 23C. Display screen 2335 indicates to the user the pump is waiting for input from the user. The user must clear the alarm and provide the necessary input before the infusion scheduled on channel A may be started by pressing Start 2340. The ability for a user to navigate quickly to the cause of the alarm improves efficiency of the user as well as workflow. Additionally, the ability to navigate directly to the cause of the alarm decreases or eliminates errors that may occur if the user had to take many steps to navigate to the appropriate display screen.

Figure 24:
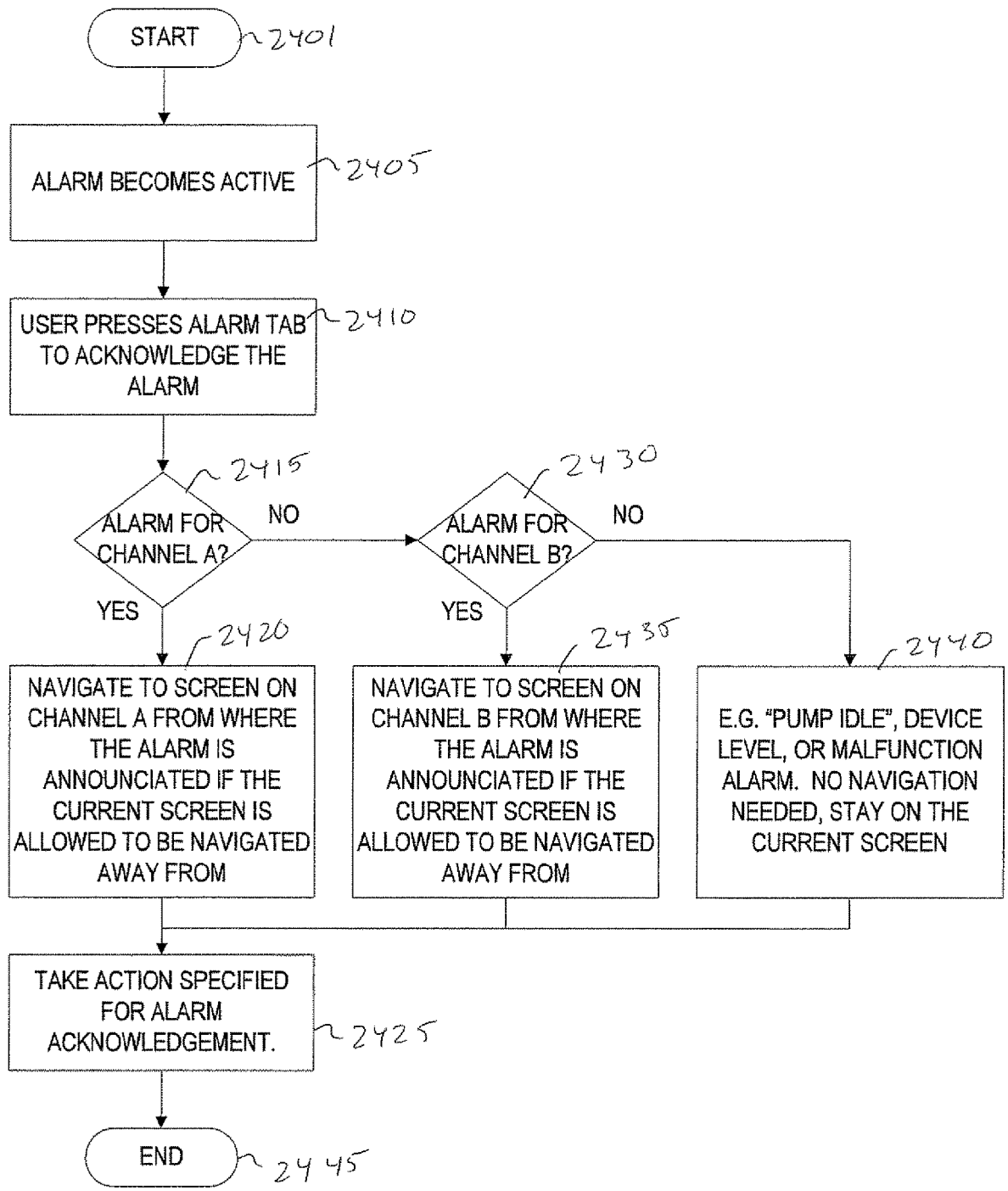
FIG. 24 is a flow chart for a program for determining a screen view display parameter based on the alarm navigation shortcut buttons, in accordance with the present invention.

With reference to FIG. 24, a flow chart for one embodiment for a program 2400 for navigating directly to a cause of an alarm is shown in accordance with the present invention. Program 2400 begins at block 2401 and proceeds to block 2405 where an alarm has been activated. In response to the alarm, an acknowledgement is received from the user in response to the user pressing an alarm tab in block 2410. Program 2400 determines at block 2415 whether the alarm was for channel A If yes, the program proceeds to block 2420 where the program navigates to the screen on channel A from where the alarm is arising if the current screen is allowed to be navigated away from. At block 2425, the user takes appropriate action in relation to the alarm. If, at block 2415, the program determines that the alarm is not for channel A, program 2400 proceeds to block 2430 where it is determined whether the alarm is for channel B. If yes, the program proceeds to block 2435 where the program navigates to the screen on channel B from where the alarm is arising if the current screen is allowed to be navigated away from. If at block 2430, the alarm is not for channel B, program 2400 proceeds to block 2440. At block 2440, the program determines that no navigation is required and proceeds to block 2425 where the user is instructed to take a specific action. Program 2400 ends at 2445.

In another embodiment of the present invention, the drug library may be configured to allow for a dose back calculation during the programming of an infusion delivery. During the programming of an infuser for a dose-based therapy (e.g. weight or BSA based therapy), the user must enter the dose first before being allowed to enter the rate. In certain clinical scenarios it is preferable for the user to enter the rate first and the dose is calculated from the rate. Providing this flexibility to the user and the hospital administration allows for increased efficiency and better work flow.

Figure 25:
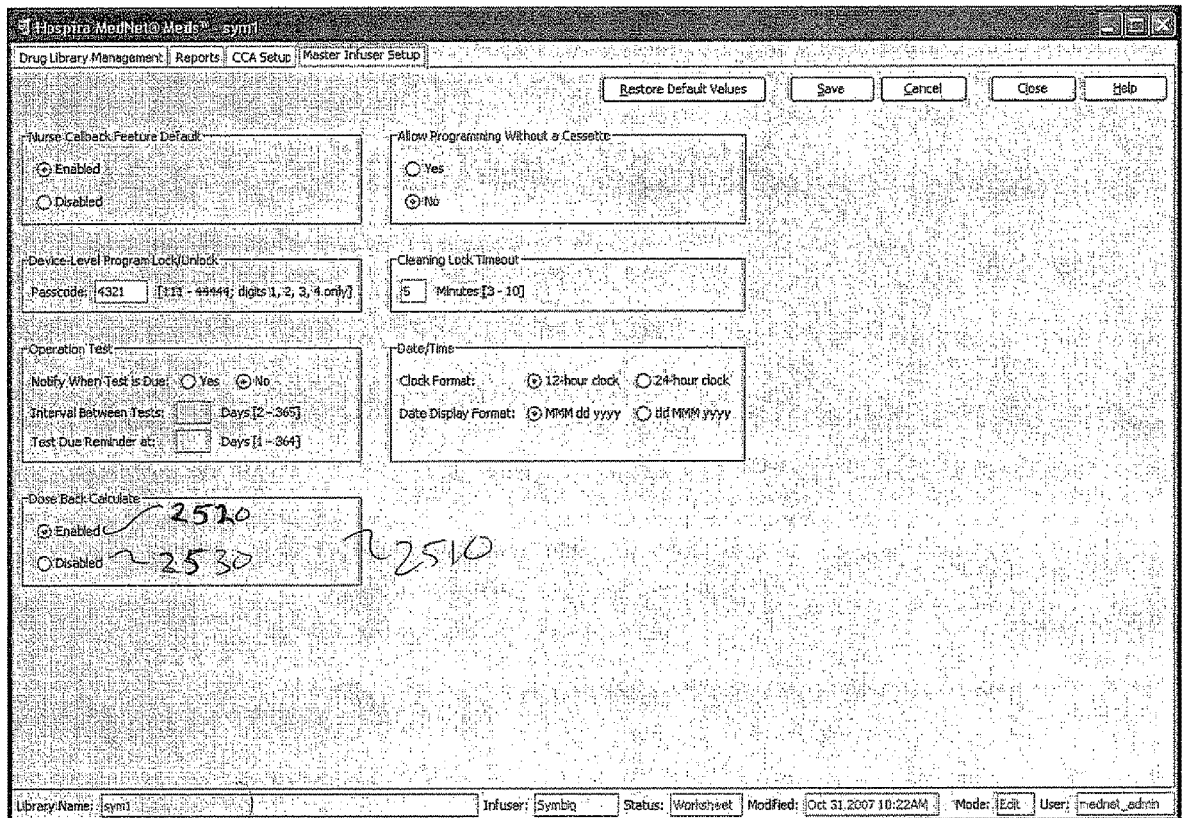
FIG. 25 is a screen shot of a graphical user interface for configuring a dose back calculation parameter at the drug library, in accordance with the present invention.

FIG. 25 illustrates a graphical user interface 2500 for configuring a drug library. A default "dose back calculate" can be set at 2510. To enable the dose back calculation at the medical device, an administrator selects "enabled" 2520. To disable the dose back calculation at the medical device, the administrator selects "disabled" 2530.

Figure 26A:
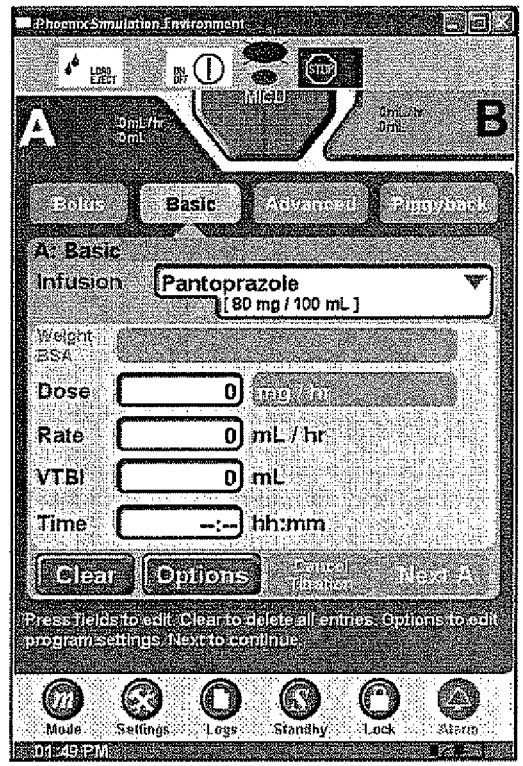
FIGS. 26A and 26B are screen shots of a graphical user interface for configuring a dose back calculation at the medical device, in accordance with the present invention.
Figure 26B:
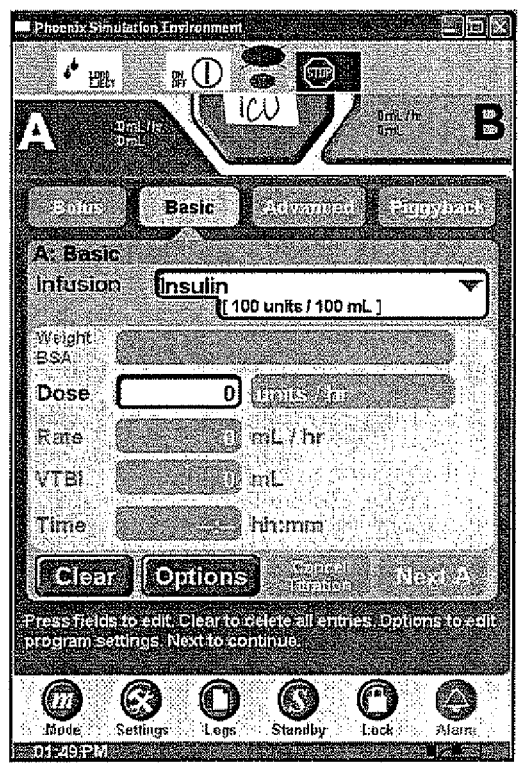

FIG. 26A is a screen shots of a medical device that allows for the dose back calculation as determined within the drug library. The user is allowed to enter dose, rate, etc. in any order as further described below. FIG. 26B is a screen shot of a medical device that disallows for the dose back calculation as determined within the drug library. The user is forced by the user interface to enter the dose first.

Figure 27:
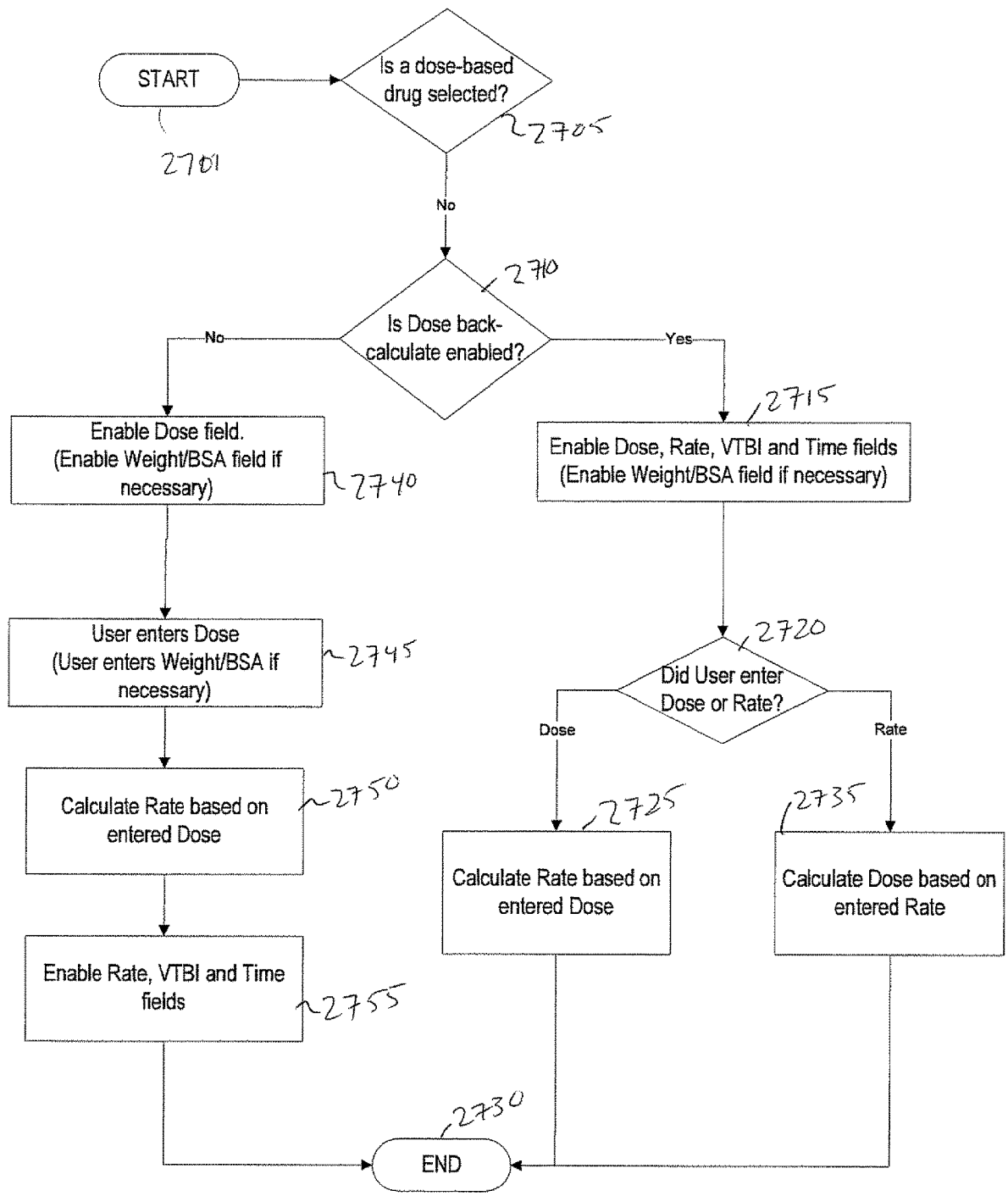
FIG. 27 is a flow chart for a program for allowing or disallowing a dose back calculation at the medical device, in accordance with the present invention.

With reference to FIG. 27, illustrated is a flow chart of a program 2700 residing in the medical device for programming a drug and calculating a dose. Program 2700 begins at 2701 and proceeds to block 2705 where the program determines if the user selected a dose-based drug. If not, program 2700 proceeds to block 2710 where program 2700 determines whether the dose back calculation is enabled at the drug library. If yes, program 2700 proceeds to block 2715, where program 2700 enables dose, rate, VTBI, time and/or weight/BSA fields. Program 2700 proceeds to 2720 where it is determined whether the user entered the dose or the rate. If dose, program 2700 proceeds to block 2725 to calculate rate based on the provided dose. If rate, program 2700 proceeds to block 2735 to calculate the dose based on the provided rate.

If at block 2710 the dose-back calculation is not enabled, program 2700 proceeds to block 27 40 where program 2700 enables a dose field as well as weight/BSA if required. Program 2700 proceeds to block 27 45 where a dose is provided as well as weight/BSA if required. Next, a rate is calculated based on the entered dose. Program 2700 proceeds to block 2755 where rate, VTBI and time fields are enabled. Program 2700 ends at 2730.

One skilled in the art will appreciate from this disclosure that the functionality shown in the figures and described herein is made possible by computer program code, and as such those features could be combined, distributed or shared among the processors of the pump 14, the MMU 12, or other computers within the healthcare facility without detracting from the present invention. Those skilled in the art will also recognize from this disclosure that selecting the CCA and providing other information or input can be done via scanning or passively receiving input from drug containers, a patient identifier, a nurse identifier or other similar items.

While the embodiments of the invention disclosed herein are presently considered to be preferred, various changes and modifications can be made without departing from the scope of the invention. The scope of the invention is indicated in the appended claims, and all changes and modifications that come within the meaning and range of equivalents are intended to be embraced therein.

What is claimed is:

1. A method of managing an infusion pump system, the method comprising:
    scanning a first barcode securely attached to a patient;
    scanning a second barcode on a medication container associated with the patient;
    generating a third barcode for display on a display screen of the infusion pump based on a patient identifier associated with the patient, said patient identifier determined based on the scanned first barcode, wherein the infusion pump is located in a first clinician care area, wherein the third barcode includes dynamically generated identifying information for a second clinician care area;
    selecting the second clinician care area for the infusion pump based at least on scanning the third barcode while the infusion pump is providing infusion to the patient;
    determining that the second clinician care area is equivalent or not equivalent to the first clinician area;
    accepting the second clinician care area based on a determination that the second clinician care area is equivalent to the first clinician area or waiting for infusion to be completed based on a determination that the second clinician care area is not equivalent to the first clinician care area; and
    automatically determining workflow corresponding to a change from the first clinician care area to a second clinician care area based on an application of a decision logic on the selection, wherein the scanning of the first barcode, the second barcode and the third barcode enable association of the infusion pump with the patient and the medical container.

2. The method of claim 1, further comprising accepting the second clinician care area based on a determination that a channel is idle.

3. A system for managing an infusion pump system, the system comprising one or more hardware processors configured to:
    generate an electronic barcode for display on a display screen of the infusion pump located in a first clinician care area based on a patient identifier associated with a patient, wherein the electronic barcode includes dynamically generated identifying information for a second clinician care area;
    scan the electronic barcode to select a clinician care area while the infusion pump is providing infusion to the patient;
    determine that the first clinician care area is modified to the second clinician care area based on the scanning of the electronic barcode;
    determine whether the second clinician care area is equivalent to the first clinician care area; and
    wait for the infusion to be completed based on the determination that the second clinician care area is not equivalent to the first clinician care area.

4. The system of claim 3, wherein the one or more hardware processors are further configured to accept the second clinician care area based on a determination that the second clinician care area is equivalent to the first clinician area.

5. The system of claim 3, wherein the one or more hardware processors are configured to accept the second clinician care area based on a determination that a channel is idle.

6. The system of claim 3, wherein the identifying information further comprises pump identifying information.

7. The system of claim 3, wherein the identifying information further comprises channel information.

8. The method of claim 1, wherein the identifying information further comprises pump identifying information.

9. The method of claim 1, wherein the identifying information further comprises channel information.

* * * * *